United States Patent
Matsutani

(10) Patent No.: US 11,730,907 B2
(45) Date of Patent: Aug. 22, 2023

(54) IMAGE ANALYSIS APPARATUS, IMAGE ANALYSIS SYSTEM, AND STORAGE MEDIUM

(71) Applicant: Konica Minolta, Inc., Tokyo (JP)

(72) Inventor: Noritsugu Matsutani, Musashino (JP)

(73) Assignee: KONICA MINOLTA, INC., Tokyo (JP)

( * ) Notice: Subject to any disclaimer, the term of this patent is extended or adjusted under 35 U.S.C. 154(b) by 283 days.

(21) Appl. No.: 16/814,288

(22) Filed: Mar. 10, 2020

(65) Prior Publication Data

US 2020/0316330 A1 Oct. 8, 2020

(30) Foreign Application Priority Data

Apr. 3, 2019 (JP) .................................. 2019-071003

(51) Int. Cl.
*G06T 7/00* (2017.01)
*A61B 6/00* (2006.01)
*A61M 16/04* (2006.01)

(52) U.S. Cl.
CPC ......... *A61M 16/0488* (2013.01); *A61B 6/486* (2013.01); *A61B 6/5217* (2013.01); *G06T 7/0012* (2013.01); *G06T 2207/10124* (2013.01); *G06T 2207/30021* (2013.01)

(58) Field of Classification Search
CPC ..... A61B 6/486; A61B 6/5217; G06T 7/0012; G06T 2211/412
See application file for complete search history.

(56) References Cited

U.S. PATENT DOCUMENTS

2017/0329927 A1* 11/2017 Taherian .................. A61B 6/50

FOREIGN PATENT DOCUMENTS

JP 2015226710 A 12/2015
JP 2018-157968 A 10/2018

OTHER PUBLICATIONS

English Translation of JP2015-226710A (Year: 2015).*
Nayak et al. "Seeing Sleep: Dynamic Imaging of Upper Airway Collapse and Collapsibility in Children." IEEE Pulse, Sep./Oct. 2014, pp. 40-44 (Year: 2014).*
Murgu et al. "Tracheobronchomalacia and Excessive Dynamic Airway Collapse." Respirology (2006) 11, pp. 388-406 (Year: 2006).*
Laroia et al. "Modern Imaging of the Tracheo-Bronchial Tree." World Journal of Radiology, vol. 2, iss.7, Jul. 28, 2010, pp. 237-248 (Year: 2010).*
English translation of JP2018-157968A (Year: 2018).*
JPO, Office Action for the related Japanese Application No. 2019-071003, dated Oct. 5, 2021, with English translation.
JPO, Office Action for the related Japanese Application No. 2019-071003, dated Apr. 5, 2022, with English translation.

* cited by examiner

*Primary Examiner* — Jon Chang
(74) *Attorney, Agent, or Firm* — Lucas & Mercanti, LLP

(57) ABSTRACT

Provided is an image analysis apparatus including a hardware processor that analyzes at least one dynamic radiograph formed from a plurality of two-dimensional images acquired by radiographing dynamics of a subject including a trachea and/or a bronchus to measure a feature amount representing a stenotic state of the trachea and/or the bronchus, and estimates the stenotic state of the trachea and/or the bronchus based on a result of the measurement.

21 Claims, 12 Drawing Sheets

FIG. 3A

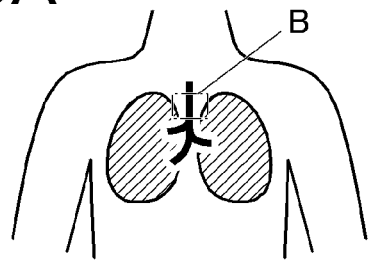

FIG. 3B

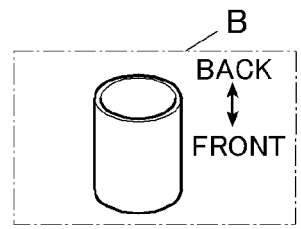

FIG. 4

| DISORDER | VIEWS OF TRACHEA/BRONCHUS | | MEASUREMENT INFORMATION OF FRONT VIEW | MEASUREMENT INFORMATION OF SIDE VIEW |
|---|---|---|---|---|
| NORMAL | SECTIONAL VIEW | FRONT VIEW / SIDE VIEW | DIAMETER: NO CHANGE<br><br>CONCENTRATION: NO CHANGE | DIAMETER: NO CHANGE<br><br>CONCENTRATION: NO CHANGE |
| TRACHEOBRON-CHOMALACIA | SABER-SHEATH TYPE<br>SECTIONAL VIEW | FRONT VIEW / SIDE VIEW | DIAMETER: REDUCED<br><br>CONCENTRATION: INCREASED | DIAMETER: EXPANDED<br><br>CONCENTRATION: DECREASED |
| | CRESCENT TYPE<br>SECTIONAL VIEW | FRONT VIEW / SIDE VIEW | DIAMETER: EXPANDED<br><br>CONCENTRATION: DECREASED | DIAMETER: REDUCED<br><br>CONCENTRATION: INCREASED |
| | CIRCUMFERENTIAL TYPE<br>SECTIONAL VIEW | FRONT VIEW / SIDE VIEW | DIAMETER: REDUCED<br><br>CONCENTRATION: DECREASED | DIAMETER: REDUCED<br><br>CONCENTRATION: DECREASED |
| EXCESSIVE DYNAMIC AIRWAY COLLAPSE | SECTIONAL VIEW | FRONT VIEW / SIDE VIEW | DIAMETER: NO CHANGE<br><br>CONCENTRATION: DECREASED | DIAMETER: REDUCED<br><br>CONCENTRATION: NO CHANGE |

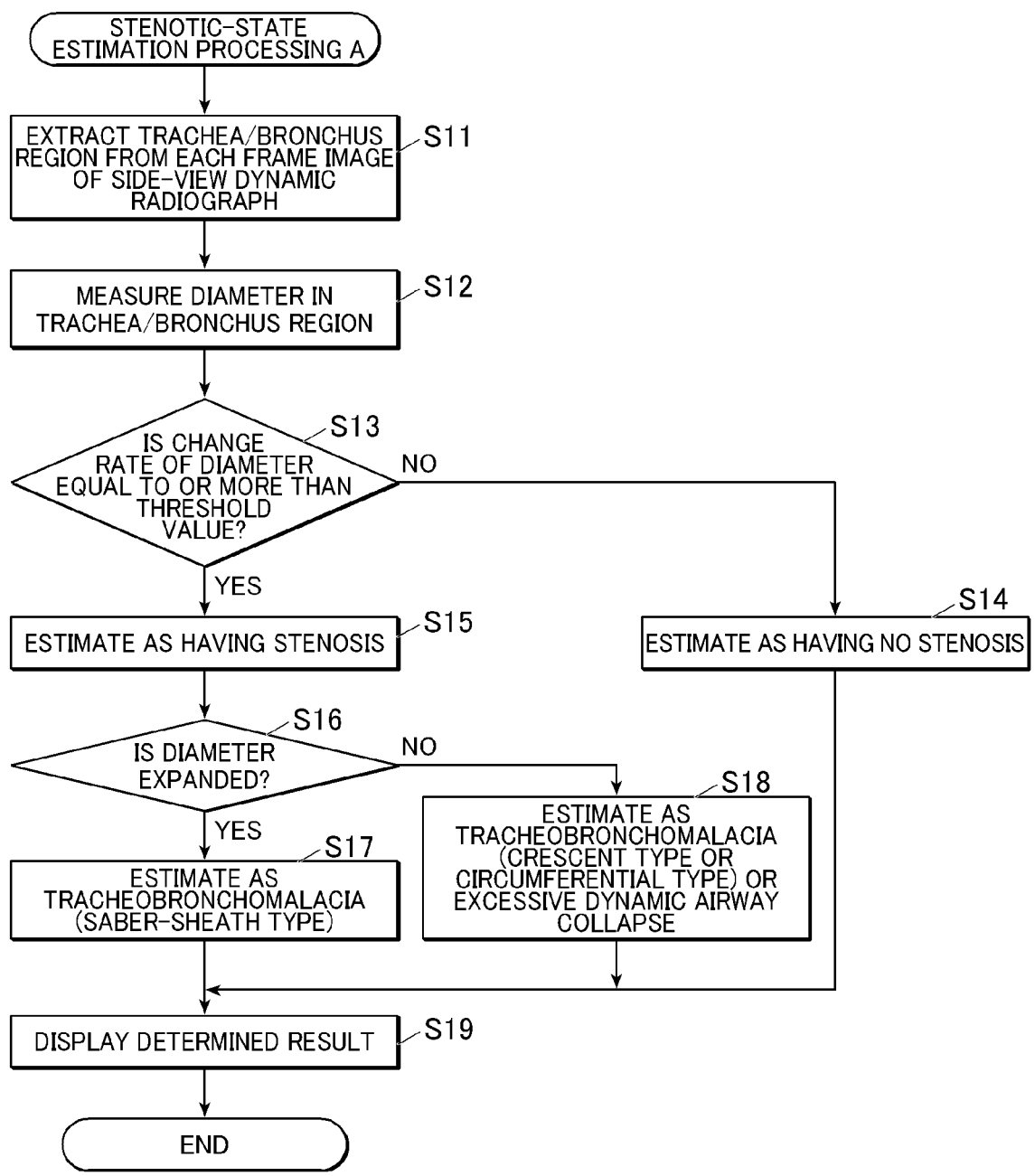

| ID | SITE | STENOSIS RATE | AREA CHANGE AMOUNT | CONCENTRATION CHANGE AMOUNT |
|---|---|---|---|---|
| 1 | TRACHEA | −35% | −10.5 | −245 |
| 2 | MAIN BRONCHUS (RIGHT LUNG) | −15% | −4.5 | −105 |
| 3 | SUPERIOR LOBE BRONCHUS (RIGHT LUNG) | −2% | −0.6 | −14 |
| 4 | BRONCHUS INTERMEDIUS (RIGHT LUNG) | +10% | +3.0 | +70 |
| 5 | MAIN BRONCHUS (LEFT LUNG) | −20% | −6 | −140 |
| 6 | SUPERIOR LOBE BRONCHUS (LEFT LUNG) | −1% | −0.3 | −7 |
| 7 | INFERIOR LOBE BRONCHUS (LEFT LUNG) | 0% | 0 | 0 |

IMAGE ANALYSIS APPARATUS, IMAGE ANALYSIS SYSTEM, AND STORAGE MEDIUM

CROSS-REFERENCE TO RELATED APPLICATIONS

The entire disclosure of Japanese Patent Application No. 2019-071003 filed on Apr. 3, 2019 is incorporated herein by reference in its entirety.

BACKGROUND

Technological Field

The present invention relates to an image analysis apparatus, an image analysis system, and a storage medium.

Description of the Related Art

Tracheobronchomalacia is known as a disorder in which an airway is constricted when exhaling due to softening of the trachea/bronchus. For evaluating tracheobronchomalacia, used is a bronchoscope that is capable of actually observing the stenotic state of the airway. However, evaluations by the bronchoscope are based only on the sense of eyesight of medical doctors, so that there is no quantitative indicators and the objectivity thereof is low. Further, even when there is a state with a stenosis, a contact of an endoscope with an airway wall may interrupt occurrence of the stenosis. While there is also a method that visualizes an airway section by a CT examination, the stenosis due to tracheobronchomalacia occurs during expiration so that it may not be able to detect the stenosis with the CT examination that requires to stop breathing. As described above, it is concerned that there may be cases where stenoses cannot be detected with conventional examination methods.

As a means for solving such problem, for example, it is disclosed in JP 2015-226710A to measure a change in the capacitance of a bronchus region based on an image acquired by a 4DCT examination that is capable of acquiring a chronological change in three-dimensional images of a subject.

SUMMARY

However, 4DCT examinations are high in the exposure dose and the cost. A simpler examination method is desired.

Objects of the present invention include being able to estimate the stenotic state of the trachea/bronchus with a simpler examination method.

To achieve at least one of the abovementioned objects, according to a first aspect of the present invention, the image analysis apparatus includes a hardware processor that:

analyzes at least one dynamic radiograph formed from a plurality of two-dimensional images acquired by radiographing dynamics of a subject including a trachea and/or a bronchus to measure a feature amount representing a stenotic state of the trachea and/or the bronchus; and estimates the stenotic state of the trachea and/or the bronchus based on a result of the measurement.

To achieve at least one of the abovementioned objects, according to a second aspect of the present invention, an image analysis system includes:

a radiographic imaging apparatus that acquires at least one dynamic radiograph formed from a plurality of two-dimensional images by radiographing dynamics of a subject including a trachea and/or a bronchus; and the image analysis apparatus.

To achieve at least one of the abovementioned objects, according to a third aspect of the present invention, an image analysis apparatus includes a hardware processor that:

analyzes a plurality of two-dimensional images acquired by continuously radiographing a subject including a trachea and/or a bronchus at a time interval shorter than a respiratory cycle to measure a feature amount representing a stenotic state of the trachea and/or the bronchus; and estimates the stenotic state of the trachea and/or the bronchus based on a result of the measurement.

To achieve at least one of the abovementioned objects, according to a fourth aspect of the present invention, an image analysis system includes:

a radiographic imaging apparatus that acquires at least one dynamic radiograph formed from a plurality of two-dimensional images by radiographing dynamics of a subject including a trachea and/or a bronchus; and the image analysis apparatus.

To achieve at least one of the abovementioned objects, according to a fifth aspect of the present invention, a non-transitory storage medium storing a program that causes a computer to:

analyze at least one dynamic radiograph formed from a plurality of two-dimensional images acquired by radiographing dynamics of a subject including a trachea and/or a bronchus to measure a feature amount representing a stenotic state of the trachea and/or the bronchus; and estimate the stenotic state of the trachea and/or the bronchus based on a result of the measurement.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention, wherein:

FIG. 3A is a schematic diagram of the chest of a human body viewed from the front;

FIG. 3B is an enlarged view of a shape cut out from the trachea surrounded by an alternate long and shot dash line in FIG. 3A;

FIG. 4 is a chart showing how the normal trachea/bronchus and the constricted tracheas/bronchi of each disorder look (sectional view, front view, side view) at the time of expiration, and changes in diameters and concentrations in a front-view dynamic radiograph and a side-view dynamic radiograph in a form of list;

FIG. 5 is a flowchart showing stenotic-state estimation processing A executed by a controller of a diagnosis console of FIG. 1;

DETAILED DESCRIPTION OF THE EMBODIMENTS

Hereinafter, one or more embodiments of the present invention will be described with reference to the drawings. However, the scope of the invention is not limited to the disclosed embodiments.

[Configuration of Image Analysis System 100]

First, a configuration of an embodiment will be described.

Figure 1:
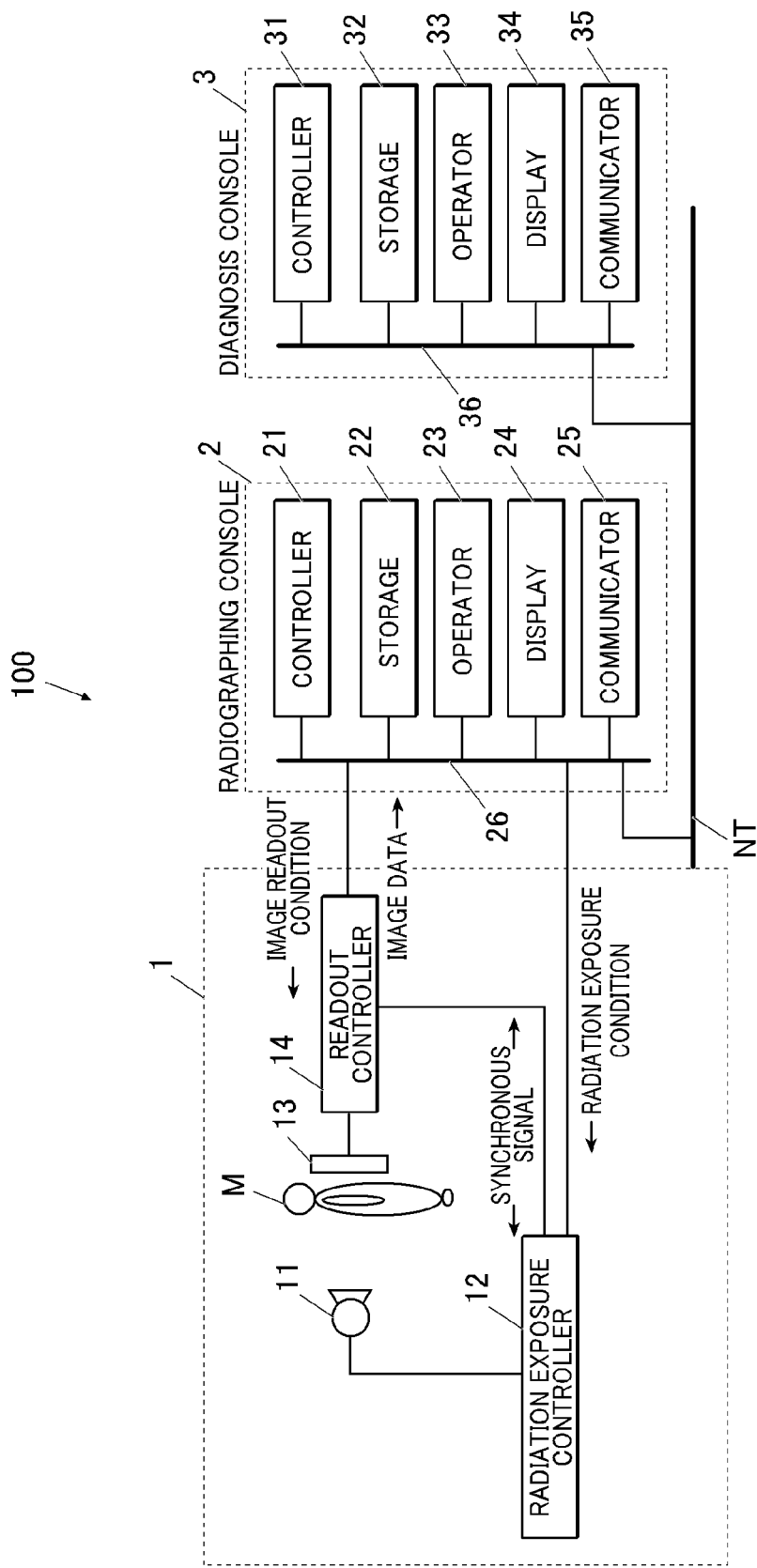
FIG. 1 is a diagram showing an entire configuration of an image analysis system according to an embodiment of the present invention.

FIG. 1 shows an entire configuration of an image analysis system 100 according to the embodiment.

As shown in FIG. 1, in the image analysis system 100, a radiographic imaging apparatus 1 and a radiographing console 2 are connected via a communication cable or the like, and the radiographing console 2 and a diagnosis console 3 are connected via a communication network NT such as LAN (Local Area Network). Each apparatus constituting the image analysis system 100 conforms to DICOM (Digital Image and Communications in Medicine) standards, and communication between each of the apparatuses is done according to DICOM.

[Configuration of Radiographic Imaging Apparatus 1]

The radiographic imaging apparatus 1 is a device for radiographing dynamics of a subject, for example. Kymography means acquisition of a plurality of images showing the dynamics of the subject by repeatedly irradiating radiations such as X-rays in a pulse form to the subject at prescribed time intervals (pulse irradiation) or irradiates radiations continuously in a low dose rate without a break (continuous irradiation). A series of images acquired by radiographing dynamics are referred to as a dynamic radiograph. Further, each of a plurality of images constituting the dynamic radiograph is referred to as a frame image. The following embodiments will be described by referring to a case where dynamics of the chest are radiographed by pulse irradiation.

A radiation source 11 is disposed at a position opposing to a radiation detector 13 with a subject M located therebetween, and irradiates a radiation (X-ray) toward the subject M according to control of a radiation exposure controller 12.

The radiation exposure controller 12 is connected to the radiographing console 2, and controls the radiation source 11 based on a radiation exposure condition input from the radiographing console 2 to perform radiographing. The radiation exposure condition input from the radiographing console 2 may be a pulse rate, a pulse width, a pulse interval, the number of radiographing frames per radiographing, a value of an X-ray tube current, a value of an X-ray tube voltage, an additional filter type, and the like, for example. The pulse rate is the number of irradiations of the radiation per second, and it is consistent with a frame rate to be described later. The pulse width is the radiation irradiating time per radiation exposure. The pulse interval is the time from the start of the first radiation exposure to the start of the next radiation exposure, and it is consistent with a frame interval to be described later.

The radiation detector 13 is made up of a semiconductor image sensor such as an FPD. The FPD has a glass substrate or the like, for example, and at prescribed positions on the substrate, arranged in matrix are a plurality of sensor elements (pixels) that detect radiations irradiated from the radiation source 11 and transmitted at least through the subject M according to the intensity, convert the detected radiations into electric signals, and accumulate the signals. Each of the pixels includes a switching device such as a TFT (Thin Film Transistor), for example. As for the FPD, while there are an indirect conversion type that converts the X-ray into electric signals with photoelectric conversion elements via a scintillator and a direct conversion type that converts the X-ray directly into electric signals, any of those may be used.

The radiation detector 13 is provided to be opposing to the radiation source 11 with the subject M interposed therebetween, A readout controller 14 is connected to the radiographing console 2. Based on an image readout condition input from the radiographing console 2, the readout controller 14 controls the switching device of each of the pixels of the radiation detector 13 to switch the electric signals accumulated in each of the pixels for readout, and reads the electric signals accumulated in the radiation detector 13 so as to acquire image data (two-dimensional images). This image data is frame images. Each frame image is composed of a signal value representing the concentration of each pixel. Further, the readout controller 14 outputs the acquired frame images to the radiographing console 2. The image readout condition may be a frame rate, a frame interval, a pixel size, an image size (matrix size), and the like, for example. The frame rate is the number of frame images acquired per second, and it is consistent with the pulse rate. The frame interval is the time from the start of one acquiring action for the frame image to the start of the next acquiring action for the frame image, and it is consistent with the pulse interval.

Note here that the radiation exposure controller 12 and the readout controller 14 are connected to each other, and mutually exchange synchronous signals to align the radiation exposure action with the image readout action.

[Configuration of Radiographing Console 2]

The radiographing console 2 controls radiographing done by the radiographic imaging apparatus 1 and readout actions of the radiographs by outputting the radiation exposure condition and the image readout condition to the radiographic imaging apparatus 1, and displays the dynamic radiograph acquired by the radiographic imaging apparatus 1 for allowing a person who is conducting radiographing such as a radiological technologist or the like to check the positioning and to check whether or not those images are suited for diagnosis.

As shown in FIG. 1, the radiographing console 2 includes a controller 21, a storage 22, an operator 23, a display 24, and a communicator 25, and each of those components is connected via a bus 26.

The controller 21 is made up of a CPU (Central Processing Unit), a RAM (Random Access Memory), and the like. The CPU of the controller 21 reads various kinds of processing programs such as a system program stored in the storage 22 according to operations made via the operator 23, expands the programs within the RAM, and executes the various kinds of processing such as radiographing control processing to be described later according to the expanded programs to perform centralized control of actions of each component of the radiographing console 2 as well as the radiation exposure actions and readout actions of the radiographic imaging apparatus 1.

The storage 22 is made up of a nonvolatile semiconductor memory, a hard disc, or the like. The storage 22 stores the various kinds of programs executed by the controller 21, parameters necessary for executing the processing by the programs, or data of processing results, and the like. For example, the storage 22 stores the program for executing the radiographing control processing shown in FIG. 2. Further, the storage 22 stores the radiation exposure condition and the readout condition by associating with an examination target site (the chest in this case) and radiographing directions (front, side). The various kinds of programs are stored in a form of readable program codes, and the controller 21 successively executes actions according to the program codes.

The operator 23 is made up of a keyboard including cursor keys, numeric input keys, various kinds of functional keys, and the like, as well as a pointing device such as a mouse, and outputs instruction signals input by key operations made via the keyboard or by mouse operations to the controller 21. Further, the operator 23 may include a touch panel on a display screen of the display 24 and, in this case, outputs instruction signals input via the touch panel to the controller 21.

The display 24 is made up of a monitor such as an LCD (Liquid Crystal Display), a CRT (Cathode Ray Tube), or the like, and displays input instructions from the operator 23, data, and the like according to instructions of display signals input from the controller 21.

The communicator 25 includes a LAN adapter, a modem, a TA (Terminal Adapter), or the like, and controls transmission/reception of data among each of apparatuses connected to a communication network NT.

[Configuration of Diagnosis Console 3]

The diagnosis console 3 is an apparatus that acquires a dynamic radiograph from the radiographing console 2, measures a feature amount representing a stenotic state of the trachea and/or bronchus (hereinafter, referred to as the trachea/bronchus) based on the acquired a dynamic radiograph, and estimates the stenotic state of the trachea/bronchus based on a result of the measurement.

As shown in FIG. 1, the diagnosis console 3 includes a controller 31 (hardware processor), a storage 32, an operator 33, a display 34, and a communicator 35, and each component is connected via a bus 36.

The controller 31 is made up of a CPU, a RAM, and the like. The CPU of the controller 31 reads various kinds of processing programs such as a system program stored in the storage 32 according to operations made via the operator 33, expands the programs within the RAM, and executes the various kinds of processing such as stenotic-state estimation processing A to F to be described later according to the expanded programs to perform centralized control of actions of each component of the diagnosis console 3.

The storage 32 is made up of a nonvolatile semiconductor memory, a hard disc, or the like. The storage 32 stores the various kinds of programs such as the program for executing, by the controller 31, the stenotic-state estimation processing A to F to be described later, parameters necessary for executing the processing by the programs, or data of processing results, and the like. Those various kinds of programs are stored in a form of readable program codes, and the controller 31 successively executes actions according to the program codes.

Further, the storage 32 stores dynamic radiographs radiographed in the past, stenosis rates (details thereof will be described later) of the trachea/bronchus measured from the dynamic radiographs, the estimated results regarding presence of stenosis and disorders by associating with patient information (for example, patient ID, name of the patient, height, weight, age, sex, and the like), and examination information (for example, examination ID, examination date, examination target site (herein, the chest), and radiographing directions (front, side)).

The operator 33 is made up of a keyboard including cursor keys, numeric input keys, various kinds of functional keys, and the like, as well as a pointing device such as a mouse, and outputs instruction signals input by key operations made by the user via the keyboard or by mouse operations to the controller 31. Further, the operator 33 may include a touch panel on a display screen of the display 34 and, in this case, outputs instruction signals input via the touch panel to the controller 31.

The display 34 is made up of a monitor such as an LCD, a CRT, or the like, and provides various kinds of displays according to instructions of display signals input from the controller 31.

The communicator 35 includes a LAN adapter, a modem, a TA, or the like, and controls transmission/reception of data among each of apparatuses connected to the communication network NT.

[Actions of Image Analysis System 100]

Next, actions of the image analysis system 100 according to the embodiment will be described.

(Actions of Radiographic Imaging Apparatus 1 and Radiographing Console 2)

First, radiographing actions of the radiographic imaging apparatus 1 and the radiographing console 2 will be described.

Figure 2:
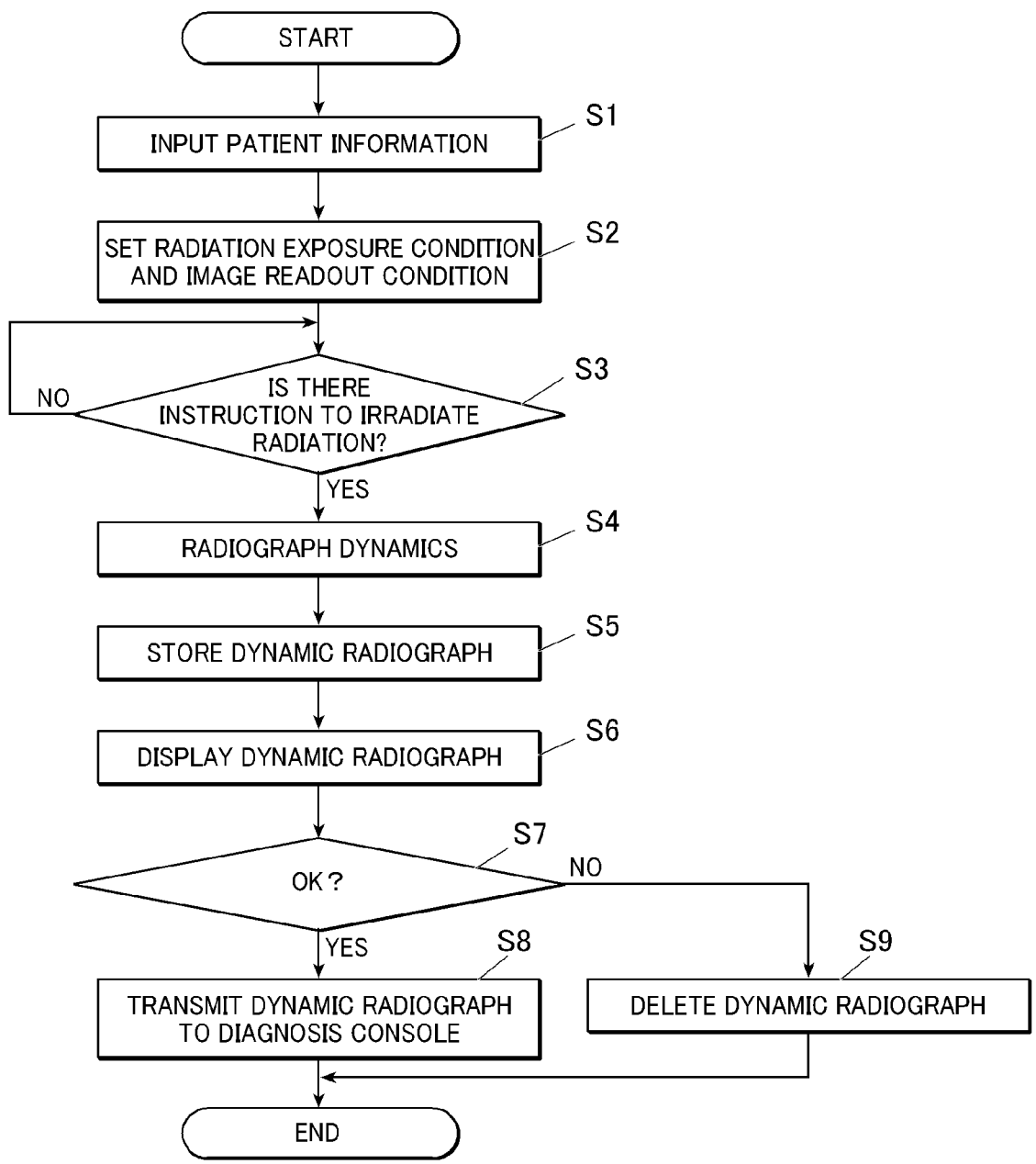
FIG. 2 is a flowchart showing radiographing control processing executed by a controller of a radiographing console in FIG. 1.

FIG. 2 shows the radiographing control processing executed by the controller 21 of the radiographing console 2. The radiographing control processing is executed by the controller 21 in cooperation with the program stored in the storage 22.

First, the operator 23 of the radiographing console 2 is operated by the person conducting radiography to input the patient information of a subject (subject M) and the examination information (step S1).

Then, the radiation exposure condition is read from the storage 22 and set in the radiation exposure controller 12, and the image readout condition is read from the storage 22 and set in the readout controller 14 (step S2). Note here that the frame rate is set to be shorter than the respiratory cycle. While the frame rate in typical kymography is 15 fps, it may be set as 7.5 fps since the respiratory cycle has a long period.

Then, it is waited for an instruction for radiation exposure by an operation made via the operator 23 (step S3).

Here, the person conducting radiography places the subject M between the radiation source 11 and the radiation detector 13 and aligns the position. Further, the person conducting radiography gives an instruction to the subject (subject M) regarding a breathing state. Specifically, the person conducting radiography gives an instruction to the subject (subject M) to relax and encourage to be under eupnea. The person conducting radiography may give an instruction to the subject (subject M) to take a deep breath. At the point where preparations for radiographing are completed, the operator 23 is operated to input a radiation exposure instruction.

If the radiation exposure instruction is input via the operator 23 (YES in step S3), a radiographing start instruction is output to the radiation exposure controller 12 and the readout controller 14 so that kymography is started (step S4). That is, a radiation is irradiated by the radiation source 11 at the pulse interval set in the radiation exposure controller 12, and frame images are acquired by the radiation detector 13.

If a radiation exposure end instruction is input via the operator 23, the controller 21 outputs an instruction for ending the radiographing to the radiation exposure controller 12 and the readout controller 14 to stop the radiographing action.

The person conducting radiography gives an instruction to end the radiation exposure such that the dynamics are radiographed at a timing including at least the expiratory level. This is because a stenosis of the trachea/bronchus occurs during expiration.

The frame images acquired by radiographing are sequentially input to the radiographing console 2, stored in the storage 22 by being associated with the numbers (frame numbers) showing the radiographed order (step S5), and displayed on the display 24 (step S6). The person conducting radiography checks the positioning and the like by the displayed a dynamic radiograph, and determines whether the images suited for diagnosis are acquired by the radiographing (radiographs OK) or re-radiographing is necessary (radiographs NG). Then, the person conducting radiography operates the operator 23 to input the determined result.

If the determined result indicating "radiographs OK" is input by a prescribed operation of the operator 23 (YES in step S7), information such as an identification ID for identifying the dynamic radiograph, the patient information, the examination information, the radiation exposure condition, the image readout condition, the number (frame number) indicating the radiographed order, and the like is added to each of a series of frame images acquired by the radiographing (for example, written to a header region of the image data in a DICOM format), and transmitted to the diagnosis console 3 via the communicator 25 (step S8). Then, the processing is ended. In the meantime, if the determined result indicating "radiographs NG" is input by a prescribed operation of the operator 23 (NO in step S7), a series of frame images stored in the storage 22 are deleted (step S9), and the processing is ended. In this case, re-radiographing is necessary.

In the embodiment, kymography on the chest front view and/or chest side view is performed according to the radiographing control processing to acquire the dynamic radiographs of the chest front view and/or chest side view.

(Actions of Diagnosis Console 3)

Next, actions of the diagnosis console 3 will be described.

In the diagnosis console 3, upon receiving a series of frame images (the chest front view and/or chest side view) of the dynamic radiographs of the chest from the radiographing console 2 via the communicator 35, the controller 31 in cooperation with the program stored in the storage 32 executes one of the stenotic-state estimation processing A to stenotic-state estimation processing F described in the followings.

Note here that FIG. 3A is a schematic diagram of the chest of a human body viewed from the front, and FIG. 3B is an enlarged view of a shape cut out from the trachea surrounded by an alternate long and short dash line B in FIG. 3A.

The trachea is formed of cartilage and muscles. As shown in FIG. 3B, the trachea is in a tubular shape, and the front (belly) side is the cartilage while the rear (back) side is the muscle. The bronchus is branched from the trachea, which is in a tubular shape like the trachea, and both the front (belly) side and the rear (back) side are the cartilage. As the disorders caused by stenoses of the trachea/bronchus, there are tracheobronchomalacia that is a stenosis of the cartilage of the trachea/bronchus and excessive dynamic airway collapse that is a stenosis of the muscle of the trachea.

FIG. 4 is a chart showing how the normal trachea/bronchus and the constricted tracheas/bronchi of each disorder look (sectional view, front view, side view) at the time of expiration, and changes in concentrations and diameters of the trachea/bronchus region in a front-view dynamic radiograph and a side-view dynamic radiograph in a form of list.

In a radiograph (dynamic radiograph), the trachea/bronchus region is drawn with a higher concentration (blackish) as the amount of the air in the depth direction is greater, while drawn with a lower concentration (whitish) as the amount of the air in the depth direction is smaller. In a state where the trachea/bronchus are not constricted in the depth direction, the trachea/bronchus have sufficient air so that the trachea/bronchus region is drawn with a high concentration. Meanwhile, in a state where the trachea/bronchus are constricted in the depth direction, the trachea/bronchus have a small amount of air so that the trachea/bronchus region is drawn with a low concentration. That is, the concentration in the trachea/bronchus region in the dynamic radiograph is the information indicating the stenotic state of the trachea/bronchus in the depth direction. The concentration in the front view and the side view in "views of trachea/bronchus" in FIG. 4 shows the concentration of the images of the front view and the side view at the time of expiration. Further, in the radiograph, the diameter (area) of the trachea/bronchus is drawn smaller in a state where the trachea/bronchus is constricted in the left and right direction.

The normal trachea/bronchus without a stenosis has the tubular cross-sectional view as shown in FIG. 4, and both the diameter (area) of the trachea/bronchus and the concentration do not change between the front-view dynamic radiograph and the side-view dynamic radiograph.

Saber-sheath type of the tracheobronchomalacia is a disorder in which the cartilage on the front side of the trachea/bronchus is constricted, and the trachea/bronchus becomes thinner from the back side toward the front side like the point of a sword while becoming wider in the depth direction. As shown in FIG. 4, when constricted, the diameter (area) of the trachea/bronchus region is reduced and the concentration is increased in the front-view dynamic radiograph. In the side-view dynamic radiograph, the diameter (area) of the trachea/bronchus region is expanded and the concentration is decreased when constricted.

Crescent type of the tracheobronchomalacia is a disorder in which the cartilage of the trachea/bronchus in the front and rear direction is constricted and the left and right direction thereof is expanded. As shown in FIG. 4, when constricted, the diameter (area) of the trachea/bronchus region is expanded and the concentration is decreased in the front-view dynamic radiograph. In the side-view dynamic radiograph, the diameter (area) of the trachea/bronchus region is reduced and the concentration is increased when constricted.

Circumferential type of the tracheobronchomalacia is a disorder in which the cartilage of the trachea/bronchus in the front and rear as well as the left and right directions is constricted. As shown in FIG. 4, when constricted, the diameter (area) of the trachea/bronchus region is reduced and the concentration is decreased as well in the front-view dynamic radiograph. In the side-view dynamic radiograph, the diameter (area) of the trachea/bronchus region is also reduced and the concentration is decreased as well when constricted.

Excessive dynamic airway collapse is a disorder in which the muscles of the trachea hurt and are curved to the inner side. As shown in FIG. 4, when constricted, there is no change in the diameter (area) of the trachea region but the concentration is decreased in the front-view dynamic radiograph. In the side-view dynamic radiograph, the diameter (area) of the trachea region is reduced but there is no change in the concentration when constricted.

That is, the diameter (area) and the concentration in the trachea/bronchus region in the front-view dynamic radiograph and/or the side-view dynamic radiograph are feature amounts representing the stenotic state of the trachea/bronchus, and it is possible to estimate the stenotic state such as presence of stenosis in the trachea/bronchus and the position of the stenosis by measuring such feature amounts.

Further, as shown in FIG. 4, by collecting the information of the trachea/bronchus in the left and right direction as well as the depth direction viewed from the front or the side, disorders caused by the stenosis of the trachea/bronchus can be estimated. For example, by measuring the diameter or the area and the concentration in the trachea/bronchus region from the dynamic radiograph radiographed from one direction either the front or the side, the information of the trachea/bronchus in the left and right direction as well as the depth direction can be acquired and the disorder of the trachea/bronchus can be estimated. Further, by measuring the diameter or the area of the trachea/bronchus region or measuring the concentration from the dynamic radiographs radiographed both from the front and the side, the information of the trachea/bronchus in the left and right direction as well as the depth direction can be acquired and the disorder of the trachea/bronchus can be estimated.

The diagnosis console 3 executes stenotic-state estimation processing according to the radiographing direction of the dynamic radiograph received from the radiographing console 2. Note that explanations written in the followings regarding the diameter of the trachea/bronchus region are the same for the area thereof.

<Estimate Stenotic State Only from Side-View Dynamic Radiograph>

Figure 6:
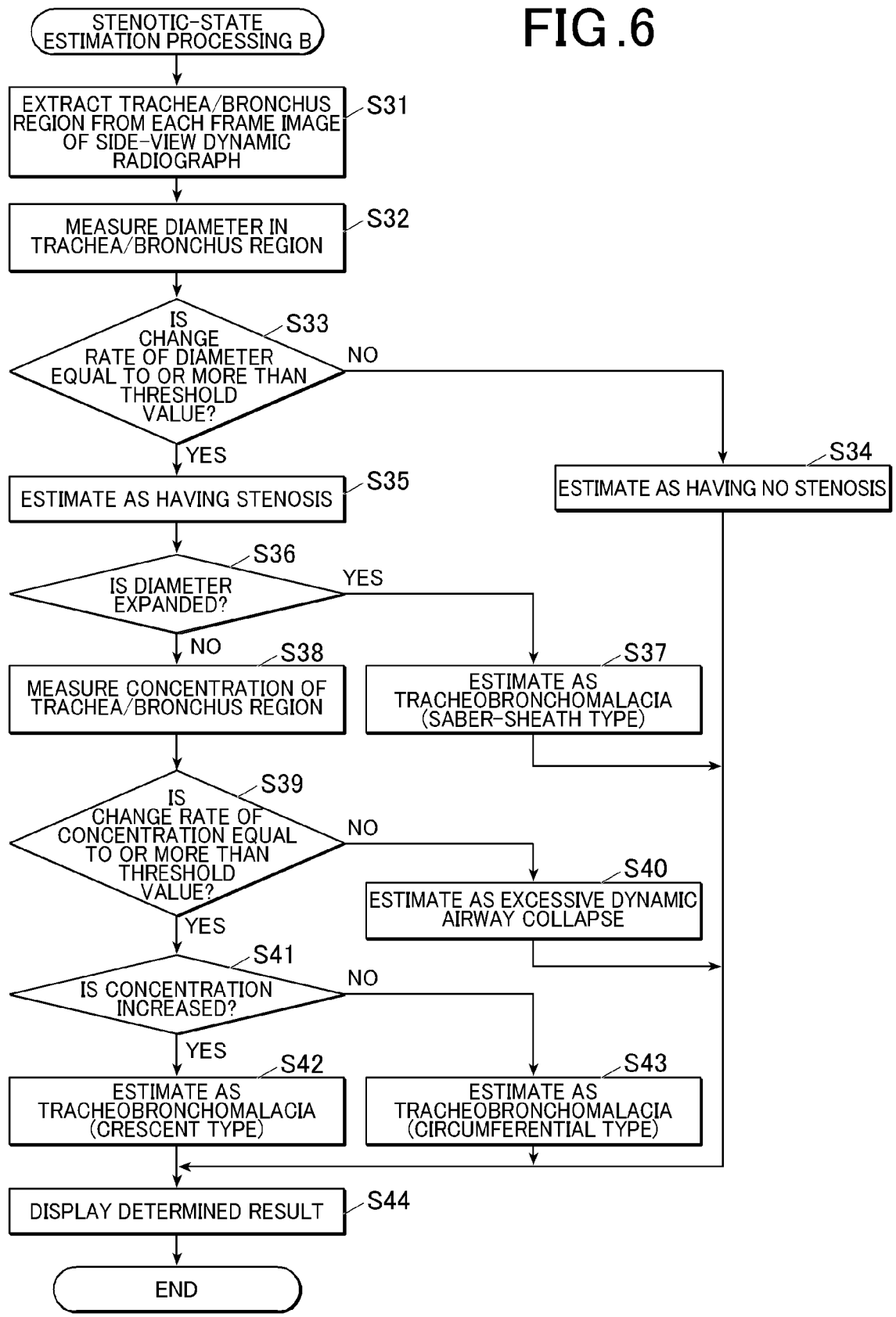
FIG. 6 is a flowchart showing stenotic-state estimation processing B executed by the controller of the diagnosis console of FIG. 1.

In a case where the dynamic radiograph received from the radiographing console 2 are only the a side-view dynamic radiograph, the controller 31 executes the stenotic-state estimation processing A shown in FIG. 5 or the stenotic-state estimation processing B shown in FIG. 6 in cooperation with the programs stored in the storage 32. The processing to be executed can be selected by the user with an operation of the operator 33.

First, the stenotic-state estimation processing A will be described by referring to FIG. 5.

First, the trachea/bronchus region is extracted from each frame image of the side-view dynamic radiograph (step S11).

The trachea/bronchus region is formed of a trachea and a plurality of bronchus regions branched therefrom (see FIG. 12) and, in step S11, the trachea/bronchus region to be an estimation target of the stenotic state is extracted from the trachea region and the plurality of bronchus region. There may be a single or a plurality of trachea/bronchus regions as the estimation target.

Extraction of the trachea/bronchus region from each frame image may be automatically done by the controller 31 or may be manually done by an operation of the user.

In a case where extraction of the trachea/bronchus region is automatically done, the trachea/bronchus region to be the estimation target may be set in advance or may be set (selected) by the user via the operator 33. The trachea/bronchus region to be the estimation target can be extracted by pattern matching processing, for example.

In a case where extraction of the trachea/bronchus region is manually done, a representative frame image (for example, the first frame image) of the received dynamic radiograph is displayed on the display 34, for example, and a region designated (traced) by the user via the operator 33 from the displayed representative frame image is extracted as the trachea/bronchus region. For the other frame images, the region designated by the user in the representative frame image is traced and extracted as the trachea/bronchus region. Alternatively, the user may set (for example, surround a region with a square or the like) an ROI (Region Of Interest) on the representative frame image displayed by the operator 33, and the pattern matching processing may be performed within that range to extract the trachea/bronchus region to be the estimation target. Alternatively, the user may add a line or an arrow to the diameter of the trachea region or the bronchus region desired to be the estimation target on the representative frame image displayed by the operator 33, the width of the line or the arrow may be taken as the diameter, and a region within a range defined in advance from the position of the diameter may be extracted as the trachea/bronchus region to be the estimation target.

In a case where the diameter is used as the feature amount representing the stenotic state in a step of a latter stage, the position of the line or the arrow drawn by the operator 33 may simply be acquired as the measurement position of the diameter of the trachea/bronchus region without extracting the trachea/bronchus region.

Then, in the trachea/bronchus region of each frame image of the received dynamic radiograph, the diameter of the trachea/bronchus region is measured as the feature amount representing the stenotic state of the trachea/bronchus (step S12). In step S12, the diameter of a position defined in advance (for example, the center part) of the trachea/bronchus region may be measured or the diameters at a plurality of positions may be measured and the representative value thereof (mean, median, or the like) may be taken as the diameter.

Then, based on the diameter of the trachea/bronchus region calculated from each frame image, the change rate of the diameter of the trachea/bronchus region is calculated and it is determined whether or not the change rate is equal to or more than a threshold value TH1 defined in advance (step S13).

The change rate of the diameter of the trachea/bronchus region can be calculated by (Expression 1).

Change rate of diameter of trachea/bronchus
region={(Dmax−Dmin)/Dmax}×100[%]   (Expression 1)

Note here that "Dmax" shows the maximum diameter among the diameters measured from each of the frame images, and "Dmin" shows the minimum diameter.

Further, in a general diagnosis, it is determined to have stenosis (abnormal) when the sectional area of the trachea (bronchus) changes by 50% or more. Therefore, on an assumption that the section of the trachea (bronchus) is a perfect circle, the sectional area of the trachea (bronchus) is "radius×radius×π" so that it is preferable to set the threshold value TH1 to be 29.3%.

If determined that the change rate of the diameter of the trachea/bronchus region is less than the threshold value TH1 defined in advance (NO in step S13), it is estimated as having no stenosis (step S14) and the processing is shifted to step S19.

If determined that the change rate of the diameter of the trachea/bronchus region is equal to or more than the threshold value TH1 defined in advance (YES in step S13), it is estimated as having a stenosis (step S15) and the processing is shifted to step S16.

In step S16, it is determined whether the diameter of the trachea/bronchus region is expanded or reduced based on the chronological change in the diameter of the trachea/bronchus region calculated from each frame image (step S16). For example, it is determined that the diameter of the trachea/bronchus region is expanded when the chronological change in the diameter of the trachea/bronchus region shows an upward convex form, while it is determined that the diameter of the trachea/bronchus region is reduced when it shows a downward convex form.

If determined that the diameter of the trachea/bronchus region is expanded (YES in step S16), it is estimated as having tracheobronchomalacia (saber-sheath type) (step S17) and the processing is shifted to step S19.

If determined that the diameter of the trachea/bronchus region is reduced (NO in step S16), it is estimated as having tracheobronchomalacia (crescent type or circumferential type) or excessive dynamic airway collapse (step S18) and the processing is shifted to step S19.

In a case where a plurality of estimation-target trachea/bronchus regions are extracted, the processing of step S12 to step S18 is executed for each region, and the processing is shifted to step S19 after completing the processing of steps S12 to S18 for all the regions.

In step S19, presence of stenosis and an estimated result of disorders are displayed on the display 34 (step S19), and the stenotic-state estimation processing A is ended.

After completing the stenotic-state estimation processing A, the measured stenosis rate of the trachea/bronchus, the presence of stenosis, and the estimated result of the disorders are stored in the storage 32 by being associated with the dynamic radiograph. Note here that the stenosis rate means the change rate of the diameter (area) and the concentration acquired in the stenotic-state estimation processing A to F, and it is shown with a plus sign when the diameter (area, concentration) is expanded (increased) and shown with a minus sign when the diameter (area, concentration) is reduced (decreased).

Next, the stenotic-state estimation processing B will be described by referring to FIG. 6.

First, the trachea/bronchus region is extracted from each frame image of the a side-view dynamic radiograph (step S31).

Processing of step S31 is the same as that described in step S11, so that the explanation thereof is to be cited.

Then, in the trachea/bronchus region of each frame image of the received dynamic radiograph, the diameter of the trachea/bronchus region is measured as the feature amount representing the stenotic state of the trachea/bronchus (step S32). The method for measuring the diameter of the trachea/bronchus region is the same as that described in step S12, so that the explanation thereof is to be cited.

Then, based on the diameter of the trachea/bronchus region calculated from each frame image, the change rate of the diameter of the trachea/bronchus region is calculated and it is determined whether or not the change rate is equal to or more than the threshold value TH1 defined in advance (step S33).

The change rate of the diameter of the trachea/bronchus region can be calculated by (Expression 1).

If determined that the change rate of the diameter of the trachea/bronchus region is less than the threshold value TH1 defined in advance (NO in step S33), it is estimated as having no stenosis (step S34) and the processing is shifted to step S44.

If determined that the change rate of the diameter of the trachea/bronchus region is equal to or more than the threshold value TH1 defined in advance (YES in step S33), it is estimated as having a stenosis (step S35) and the processing is shifted to step S36.

In step S36, it is determined whether the diameter of the trachea/bronchus region is expanded or reduced based on the chronological change in the diameter of the trachea/bronchus region calculated from each frame image (step S36). For example, it is determined that the diameter of the trachea/bronchus region is expanded when the chronological change in the diameter of the trachea/bronchus region shows an upward convex form, while it is determined that the diameter of the trachea/bronchus region is reduced when it shows a downward convex form.

If determined that the diameter of the trachea/bronchus region is expanded (YES in step S36), it is estimated as having tracheobronchomalacia (saber-sheath type) (step S37) and the processing is shifted to step S44.

If determined that the diameter of the trachea/bronchus region is reduced (NO in step S36), the concentration of the trachea/bronchus region is measured as the feature amount representing the stenotic state of the trachea/bronchus in the trachea/bronchus region of each frame image of the received dynamic radiograph (step S38).

In step S38, the signal value of the pixel at a position (for example, the center) defined in advance within the trachea/bronchus region may be measured as the concentration, for example, or a representative value (for example, mean value, median, maximum value, minimum value, or the like) of the signal values of the pixels within the trachea/bronchus region may be measured as the concentration.

Then, based on the concentration of the trachea/bronchus region calculated from each frame image, the change rate of the concentration of the trachea/bronchus region is calculated and it is determined whether or not the change rate is equal to or more than a threshold value TH2 defined in advance (step S39).

The change rate of the concentration of the trachea/bronchus region can also be calculated by an expression same as (Expression 1) with "Dmax" of (Expression 1) being the maximum concentration and "Dmin" being the minimum concentration. Further, it is preferable to set the threshold value TH2 to be the change rate of the concentration corresponding to "threshold value TH1 of diameter change rate=29.3%". The concentration fluctuates depending on the radiographic imaging apparatus and the radiographing condition, so that it is preferable to adjust the concentration by conducting experiments.

If determined that the change rate of the concentration of the trachea/bronchus region is less than the threshold value TH2 defined in advance (NO in step S39), it is estimated as having excessive dynamic airway collapse (step S40) and the processing is shifted to step S44.

If determined that the change rate of the concentration of the trachea/bronchus region is equal to or more than the threshold value TH2 defined in advance (YES in step S39), it is determined whether the concentration of the trachea/bronchus region is increased or decreased based on the chronological change in the concentration of the trachea/bronchus region calculated from each frame image (step S41). For example, it is determined that the concentration of the trachea/bronchus region is increased when the chronological change in the concentration of the trachea/bronchus region shows an upward convex form, while it is determined to be decreased when it shows a downward convex form.

If determined that the concentration of the trachea/bronchus region is increased (YES in step S41), it is estimated as having tracheobronchomalacia (crescent type) (step S42) and the processing is shifted to step S44.

If determined that the concentration of the trachea/bronchus region is decreased (NO in step S41), it is estimated as having tracheobronchomalacia (circumferential type) (step S43) and the processing is shifted to step S44.

In a case where a plurality of estimation-target trachea/bronchus regions are extracted, the processing of step S32 to step S43 is executed for each region, and the processing is shifted to step S44 after completing the processing of steps S32 to S43 for all the regions.

In step S44, presence of stenosis and an estimated result of disorders are displayed on the display 34 (step S44), and the stenotic-state estimation processing B is ended. After completing the stenotic-state estimation processing B, the measured stenosis rate of the trachea/bronchus, the presence of stenosis, and the estimated result of the disorders are stored in the storage 32 by being associated with the dynamic radiograph.

With the stenotic-state estimation processing B, the stenotic state is estimated by using both the diameter representing the stenotic state in the left and right direction and the concentration representing the stenotic state in the depth direction of the trachea/bronchus region in the side-view dynamic radiograph, so that it is possible to estimate not only the presence of stenosis but also disorders. In the stenotic-state estimation processing B described above, estimation is done based first on the change rate of the diameter of the trachea/bronchus region. However, estimation may be done based first on the change rate of the concentration.

<Estimate Stenotic State Only from Front-View Dynamic Radiograph>

Figure 7:
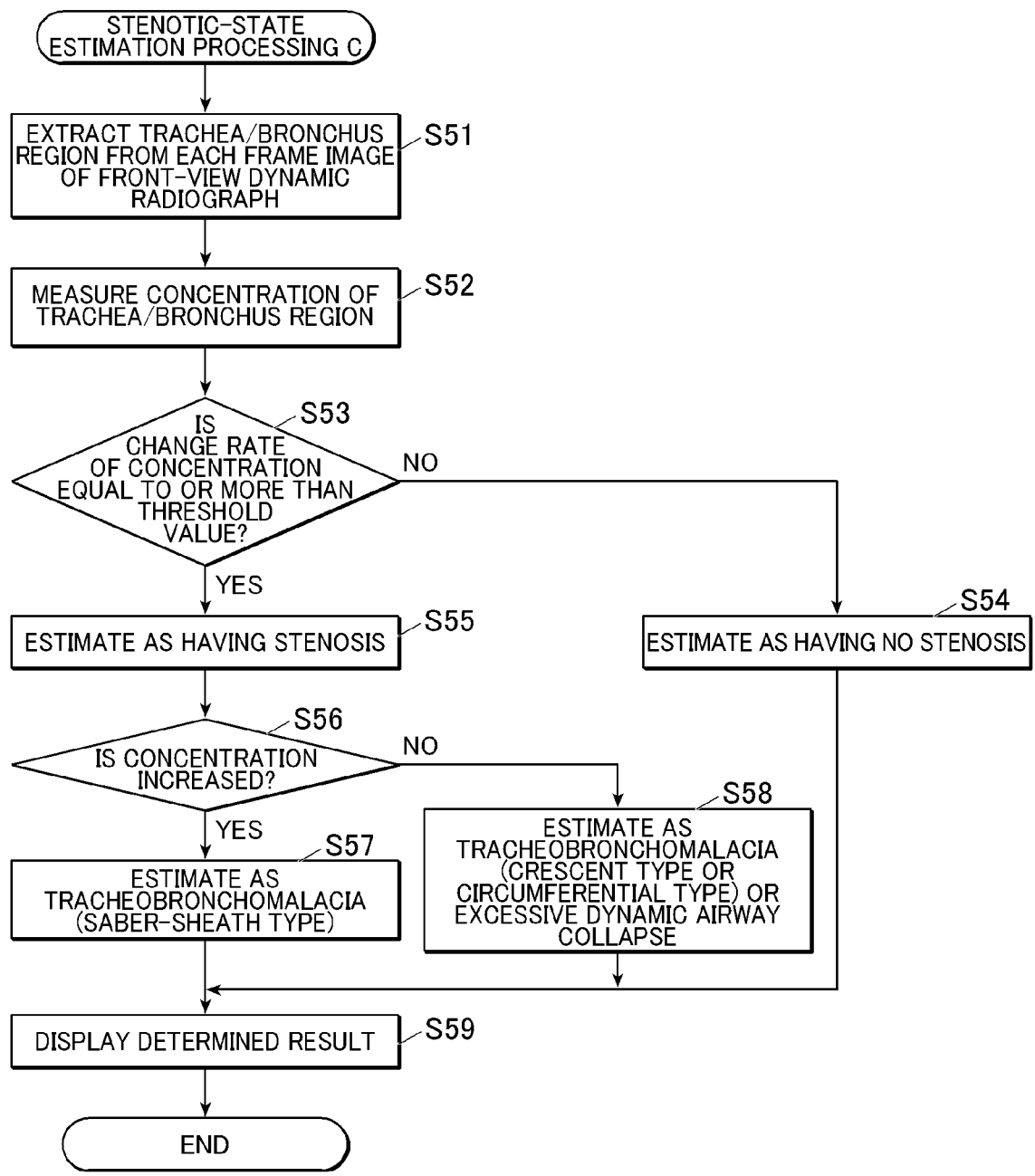
FIG. 7 is a flowchart showing stenotic-state estimation processing C executed by the controller of the diagnosis console of FIG. 1.
Figure 8:
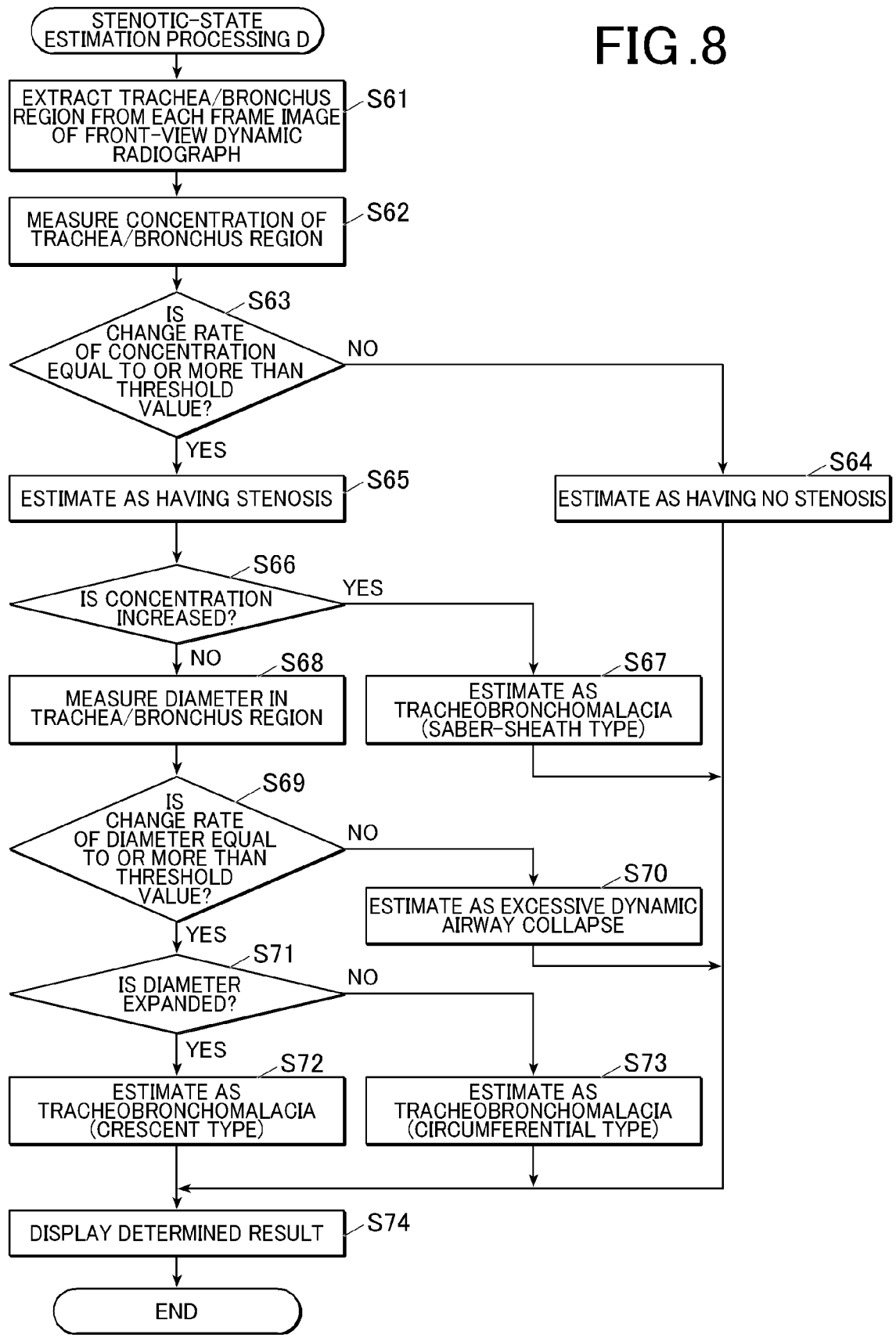
FIG. 8 is a flowchart showing stenotic-state estimation processing D executed by the controller of the diagnosis console of FIG. 1.

In a case where the dynamic radiograph received from the radiographing console 2 are only the a front-view dynamic radiograph, the controller 31 executes the stenotic-state estimation processing C shown in FIG. 7 or the stenotic-state estimation processing D shown in FIG. 8 in cooperation with the programs stored in the storage 32. The processing to be executed can be selected by the user with an operation of the operator 33.

First, the stenotic-state estimation processing C will be described by referring to FIG. 7.

First, the trachea/bronchus region is extracted from each frame image of the front-view dynamic radiograph (step S51).

Processing of step S51 is the same as that described in step S11 of FIG. 5, so that the explanation thereof is to be cited.

Then, in the trachea/bronchus region of each frame image of the received dynamic radiograph, the concentration of the trachea/bronchus region is measured as the feature amount representing the stenotic state of the trachea/bronchus (step S52). Processing of step S52 is the same as that described in step S38 of FIG. 6, so that the explanation thereof is to be cited.

Then, based on the concentration of the trachea/bronchus region calculated from each frame image, the change rate of the concentration of the trachea/bronchus region is calculated and it is determined whether or not the change rate is equal to or more than the threshold value TH2 defined in advance (step S53).

The change rate of the concentration of the trachea/bronchus region can also be calculated by an expression same as (Expression 1) with "Dmax" of (Expression 1) being the maximum concentration and "Dmin" being the minimum concentration.

If determined that the change rate of the concentration of the trachea/bronchus region is less than the threshold value TH2 defined in advance (NO in step S53), it is estimated as having no stenosis (step S54) and the processing is shifted to step S59.

If determined that the change rate of the concentration of the trachea/bronchus region is equal to or more than the threshold value TH2 defined in advance (YES in step S53), it is estimated as having a stenosis (step S55) and the processing is shifted to step S56.

In step S56, it is determined whether the concentration of the trachea/bronchus region is increased or decreased based on the chronological change in the concentration of the trachea/bronchus region calculated from each frame image (step S56). Processing of step S56 is the same as that described in step S41 of FIG. 6, so that the explanation thereof is to be cited.

If determined that the concentration of the trachea/bronchus region is increased (YES in step S56), it is estimated as having tracheobronchomalacia (saber-sheath type) (step S57) and the processing is shifted to step S59.

If determined that the concentration of the trachea/bronchus region is decreased (NO in step S56), it is estimated as having tracheobronchomalacia (crescent type or circumferential type) or excessive dynamic airway collapse (step S58) and the processing is shifted to step S59.

In a case where a plurality of estimation-target trachea/bronchus regions are extracted, the processing of step S52 to step S58 is executed for each region, and the processing is shifted to step S59 after completing the processing of steps S52 to S58 for all the regions.

In step S59, presence of stenosis and an estimated result of disorders are displayed on the display 34 (step S59), and the stenotic-state estimation processing C is ended. After completing the stenotic-state estimation processing C, the measured stenosis rate of the trachea/bronchus, the presence of stenosis, the estimated result of the disorders are stored in the storage 32 by being associated with the dynamic radiograph.

Next, the stenotic-state estimation processing D will be described by referring to FIG. 8.

First, the trachea/bronchus region is extracted from each frame image of the a front-view dynamic radiograph (step S61).

Processing of step S61 is the same as that described in step S11 of FIG. 5, so that the explanation thereof is to be cited.

Then, in the trachea/bronchus region of each frame image of the received dynamic radiograph, the concentration of the trachea/bronchus region is measured as the feature amount representing the stenotic state of the trachea/bronchus (step S62). Measurement of the concentration of the trachea/bronchus region is the same as that described in step S38 of FIG. 6, so that the explanation thereof is to be cited.

Then, based on the diameter of the trachea/bronchus region calculated from each frame image, the change rate of the concentration of the trachea/bronchus region is calculated and it is determined whether or not the change rate is equal to or more than the threshold value TH2 defined in advance (step S63).

The change rate of the concentration of the trachea/bronchus region can also be calculated by an expression same as (Expression 1) with "Dmax" of (Expression 1) being the maximum concentration and "Dmin" being the minimum concentration.

If determined that the change rate of the concentration of the trachea/bronchus region is less than the threshold value TH2 defined in advance (NO in step S63), it is estimated as having no stenosis (step S64) and the processing is shifted to step S74.

If determined that the change rate of the concentration of the trachea/bronchus region is equal to or more than the threshold value TH2 defined in advance (YES in step S63), it is estimated as having a stenosis (step S65) and the processing is shifted to step S66.

In step S66, it is determined whether the concentration of the trachea/bronchus region is increased or decreased based on the chronological change in the concentration of the trachea/bronchus region calculated from each frame image (step S66). Processing of step S66 is the same as that described in step S41 of FIG. 6, so that the explanation thereof is to be cited.

If determined that the concentration of the trachea/bronchus region is increased (YES in step S66), it is estimated as having tracheobronchomalacia (saber-sheath type) (step S67) and the processing is shifted to step S74.

If determined that the concentration of the trachea/bronchus region is decreased (NO in step S66), the diameter of the trachea/bronchus region is measured as the feature amount representing the stenotic state of the trachea/bronchus in the trachea/bronchus region of each frame image of the received dynamic radiograph (step S68).

Processing of step S68 is the same as that described in step S12 of FIG. 5, so that the explanation thereof is to be cited.

Then, based on the diameter of the trachea/bronchus region calculated from each frame image, the change rate of the diameter of the trachea/bronchus region is calculated and it is determined whether or not the change rate is equal to or more than the threshold value TH1 defined in advance (step S69).

The change rate of the diameter of the trachea/bronchus region can be calculated by (Expression 1).

If determined that the change rate of the diameter of the trachea/bronchus region is less than the threshold value TH1 defined in advance (NO in step S69), it is estimated as having excessive dynamic airway collapse (step S70) and the processing is shifted to step S74.

If determined that the change rate of the diameter of the trachea/bronchus region is equal to or more than the threshold value TH1 defined in advance (YES in step S69), it is determined whether the diameter of the trachea/bronchus region is expanded or reduced based on the chronological change in the diameter of the trachea/bronchus region calculated from each frame image (step S71).

Processing of step S71 is the same as that described in step S16 of FIG. 5, so that the explanation thereof is to be cited.

If determined that the diameter of the trachea/bronchus region is expanded (YES in step S71), it is estimated as having tracheobronchomalacia (crescent type) (step S72) and the processing is shifted to step S74.

If determined that the diameter of the trachea/bronchus region is reduced (NO in step S71), it is estimated as having tracheobronchomalacia (circumferential type) (step S73) and the processing is shifted to step S74.

In a case where a plurality of estimation-target trachea/bronchus regions are extracted, the processing of step S62 to step S73 is executed for each region, and the processing is shifted to step S74 after completing the processing of steps S62 to S73 for all the regions.

In step S74, presence of stenosis and an estimated result of disorders are displayed on the display 34 (step S74), and the stenotic-state estimation processing D is ended. After completing the stenotic-state estimation processing D, the measured stenosis rate of the trachea/bronchus, the presence of stenosis, and the estimated result of the disorders are stored in the storage 32 by being associated with the dynamic radiograph.

With the stenotic-state estimation processing D, the stenotic state is estimated by using both the diameter representing the stenotic state in the left and right direction and the concentration representing the stenotic state in the depth direction of the trachea/bronchus region in the front-view dynamic radiograph, so that it is possible to estimate not only presence of stenoses but also disorders. In the stenotic-state estimation processing D described above, estimation is done based first on the change rate of the concentration of the trachea/bronchus region. However, estimation may be done based first on the change rate of the diameter.

<Estimate Stenotic State from Front-View and Side-View Dynamic Radiographs>

Figure 9:
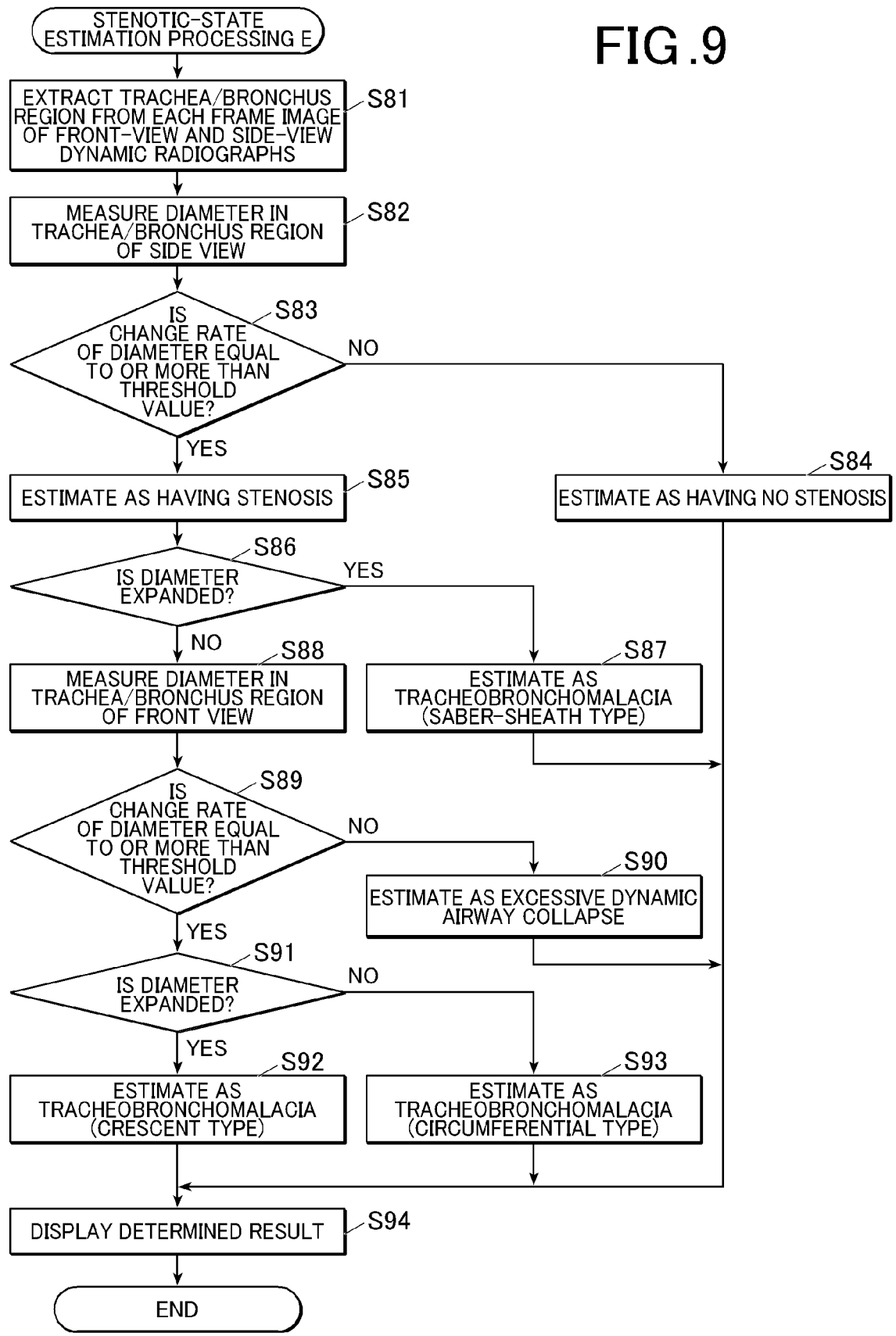
FIG. 9 is a flowchart showing stenotic-state estimation processing E executed by the controller of the diagnosis console of FIG. 1.
Figure 10:
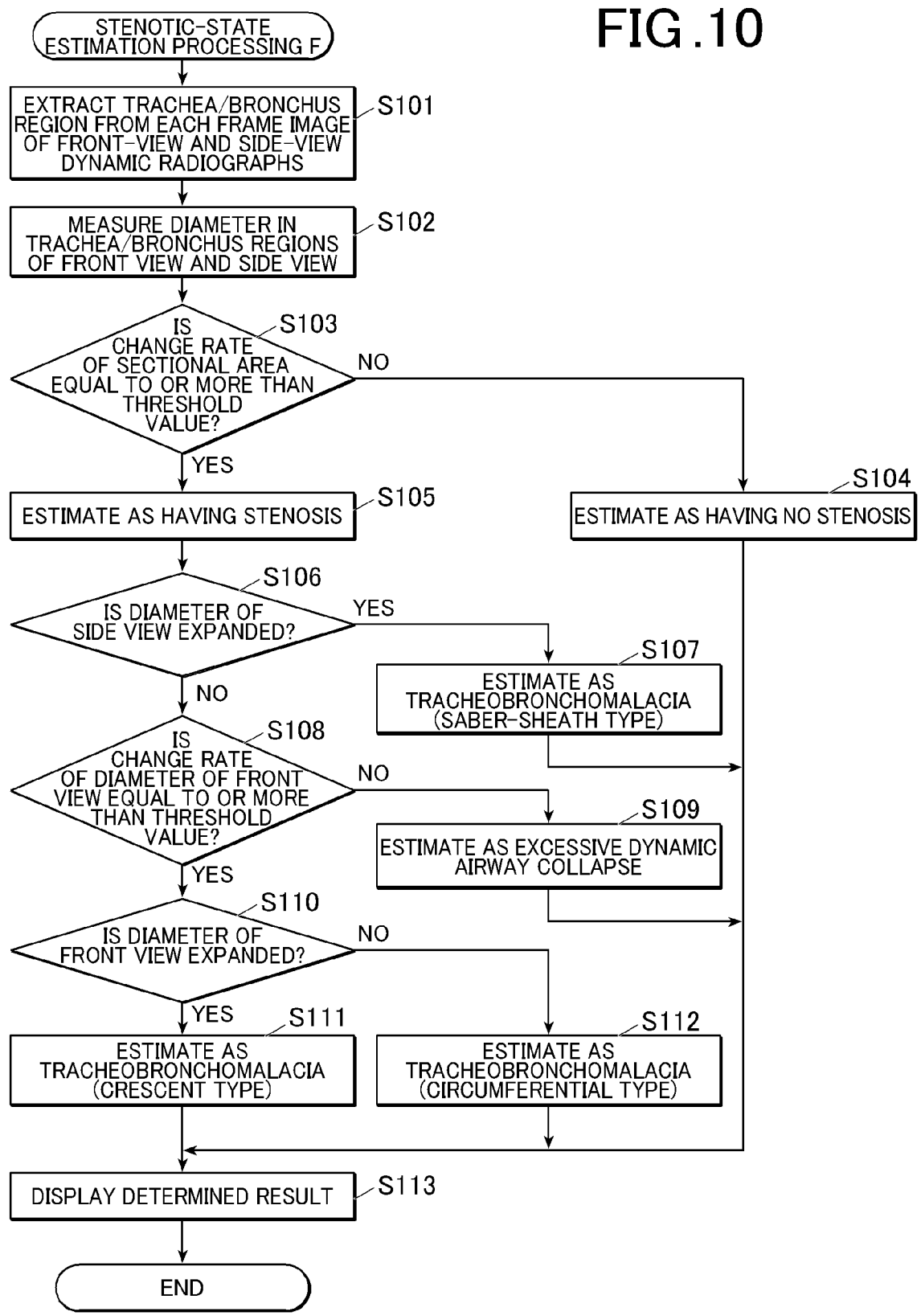
FIG. 10 is a flowchart showing stenotic-state estimation processing F executed by the controller of the diagnosis console of FIG. 1.

In a case where the dynamic radiographs received from the radiographing console 2 are the front-view and side-view dynamic radiographs, the controller 31 executes the stenotic-state estimation processing E shown in FIG. 9 or the stenotic-state estimation processing F shown in FIG. 10 in cooperation with the programs stored in the storage 32. The processing to be executed can be selected by the user with an operation of the operator 33.

First, the stenotic-state estimation processing E will be described by referring to FIG. 9.

First, the trachea/bronchus region is extracted from each frame image of the front-view and side-view dynamic radiographs (step S81).

Processing of step S81 is the same as that described in step S11 of FIG. 5, so that the explanation thereof is to be cited.

Based on the positional information of the ribs, positions of the trachea/bronchus regions as the estimation target are aligned in the corresponding frame images (the frame images radiographed at the same timing or the frame images with the closest respiratory phase) of the front-view dynamic radiograph and the side-view dynamic radiograph.

Then, in the trachea/bronchus region of each frame image of the side-view dynamic radiograph, the diameter of the trachea/bronchus region is measured as the feature amount representing the stenotic state of the trachea/bronchus (step S82). Processing of step S82 is the same as that described in step S12 of FIG. 5, so that the explanation thereof is to be cited.

Then, based on the diameter of the trachea/bronchus region calculated from each frame image of the side-view dynamic radiograph, the change rate of the diameter of the trachea/bronchus region is calculated and it is determined whether or not the change rate is equal to or more than a threshold value TH1 defined in advance (step S83).

The change rate of the diameter of the trachea/bronchus region can be calculated by (Expression 1).

If determined that the change rate of the diameter of the trachea/bronchus region in the side view is less than the threshold value TH1 defined in advance (NO in step S83), it is estimated as having no stenosis (step S84) and the processing is shifted to step S94.

If determined that the change rate of the diameter of the trachea/bronchus region in the side view is equal to or more than the threshold value TH1 defined in advance (YES in step S83), it is estimated as having a stenosis (step S85) and the processing is shifted to step S86.

In step S86, it is determined whether the diameter of the side-view trachea/bronchus region is expanded or reduced based on the chronological change in the diameter of the trachea/bronchus region calculated from each frame image of the side-view dynamic radiograph (step S86). Processing of step S86 is the same as that described in step S16 of FIG. 5, so that the explanation thereof is to be cited.

If determined that the diameter of the trachea/bronchus region in the side view is expanded (YES in step S86), it is estimated as having tracheobronchomalacia (saber-sheath type) (step S87) and the processing is shifted to step S94.

If determined that the diameter of the trachea/bronchus region in the side view is reduced (NO in step S86), the diameter of the trachea/bronchus region is measured as the feature amount representing the stenotic state of the trachea/bronchus in the trachea/bronchus region of each frame image of the front-view dynamic radiograph (step S88). Processing of step S88 is the same as that described in step S12 of FIG. 5, so that the explanation thereof is to be cited.

Then, based on the diameter of the trachea/bronchus region calculated from each frame image of the front-view dynamic radiograph, the change rate of the diameter of the trachea/bronchus region in the front view is calculated and it is determined whether or not the change rate is equal to or more than the threshold value TH1 defined in advance (step S89).

The change rate of the diameter of the trachea/bronchus region can be calculated by (Expression 1).

If determined that the change rate of the diameter of the trachea/bronchus region in the front view is less than the threshold value TH1 defined in advance (NO in step S89), it is estimated as having excessive dynamic airway collapse (step S90) and the processing is shifted to step S94.

If determined that the change rate of the diameter of the trachea/bronchus region in the front view is equal to or more than the threshold value TH1 defined in advance (YES in step S89), it is determined whether the diameter of the trachea/bronchus region is expanded or reduced based on the chronological change in the diameter of the trachea/bronchus region calculated from each frame image of the front-view dynamic radiograph (step S91). Processing of step S91 is the same as that described in step S16 of FIG. 5, so that the explanation thereof is to be cited.

If determined that the diameter of the trachea/bronchus region of the front view is expanded (YES in step S91), it is estimated as having tracheobronchomalacia (crescent type) (step S92) and the processing is shifted to step S94.

If determined that the diameter of the trachea/bronchus region of the front view is reduced (NO in step S91), it is estimated as having tracheobronchomalacia (circumferential type) (step S93) and the processing is shifted to step S94.

In a case where a plurality of estimation-target trachea/bronchus regions are extracted, the processing of step S82 to step S93 is executed for each region, and the processing is shifted to step S94 after completing the processing of steps S82 to S93 for all the regions.

In step S94, presence of stenosis and an estimated result of disorders are displayed on the display 34 (step S94), and the stenotic-state estimation processing E is ended. After completing the stenotic-state estimation processing E, the measured stenosis rate of the trachea/bronchus, the presence of stenosis, and the estimated result of the disorders are stored in the storage 32 by being associated with the dynamic radiograph.

Note that it is possible with the stenotic-state estimation processing E to estimate the presence of stenosis and disorders in a similar manner even when the front view and the side view are switched and the diameter is replaced with the concentration.

Next, the stenotic-state estimation processing F will be described by referring to FIG. 10.

First, the trachea/bronchus region is extracted from each frame image of the front-view and side-view dynamic radiographs (step S101).

Processing of step S101 is the same as that described in step S11 of FIG. 5, so that the explanation thereof is to be cited.

Based on the positional information of the ribs, positions of the trachea/bronchus regions as the estimation target are aligned in the corresponding frame images (the frame images radiographed at the same timing or the frame images with the closest respiratory phase) of the front-view dynamic radiograph and the side-view dynamic radiograph.

Then, in the trachea/bronchus region of each frame image of the front-view and side-view dynamic radiographs, the diameter of the trachea/bronchus region is measured as the feature amount representing the stenotic state of the trachea/bronchus (step S102). Processing of step S102 is the same as that described in step S12 of FIG. 5, so that the explanation thereof is to be cited.

Then, based on the diameter of the trachea/bronchus region calculated from each frame image of the front-view and side-view dynamic radiographs, the change rate of the sectional area of the trachea/bronchus region is calculated and it is determined whether or not the change rate is equal to or more than a threshold value TH3 defined in advance (step S103).

On an assumption that the section of the trachea/bronchus region is an ellipse, the sectional area of the trachea/bronchus region is expressed as "semi-minor axis×semi-major axis×π". That is, the sectional area can be calculated by calculating "(front-view diameter÷2)×(side-view diameter÷2)×π". The change rate of the sectional area of the trachea/bronchus region can be calculated by substituting the maximum sectional area to "Dmax" of (Expression 1) and the minimum sectional area to "Dmin".

Further, in a general diagnosis, it is determined to have a stenosis (abnormal) when the sectional area of the trachea (bronchus) changes by 50% or more. Therefore, it is preferable to set the threshold value TH3 to be 50%.

If determined that the change rate of the sectional area of the trachea/bronchus region is less than the threshold value TH3 defined in advance (NO in step S103), it is estimated as having no stenosis (step S104) and the processing is shifted to step S113.

If determined that the change rate of the sectional area of the trachea/bronchus region is equal to or more than the threshold value TH3 defined in advance (YES in step S103), it is estimated as having a stenosis (step S105) and the processing is shifted to step S106.

In step S106, it is determined whether the diameter of the trachea/bronchus region in the side view is expanded or reduced based on the chronological change in the diameter of the trachea/bronchus region calculated from each frame image of the side-view dynamic radiograph (step S106). Processing of step S106 is the same as that described in step S16 of FIG. 5, so that the explanation thereof is to be cited.

If determined that the diameter of the trachea/bronchus region in the side view is expanded (YES in step S106), it is estimated as having tracheobronchomalacia (saber-sheath type) (step S107) and the processing is shifted to step S113.

If determined that the diameter of the trachea/bronchus region in the side view is reduced (NO in step S106), based on the diameter of the trachea/bronchus region calculated from each frame image of the front-view dynamic radiograph, the change rate of the diameter of the trachea/bronchus region is calculated to determine whether or not it is equal to or more than the threshold value TH1 defined in advance (step S108).

The change rate of the diameter of the trachea/bronchus region can be calculated by (Expression 1).

If determined that the change rate of the diameter of the trachea/bronchus region in the front view is less than the threshold value TH1 defined in advance (NO in step S108), it is estimated as having excessive dynamic airway collapse (step S109) and the processing is shifted to step S113.

If determined that the change rate of the diameter of the trachea/bronchus region in the front view is equal to or more than the threshold value TH1 defined in advance (YES in step S108), it is determined whether the diameter of the trachea/bronchus region is expanded or reduced based on the chronological change in the diameter of the trachea/bronchus region calculated from each frame image of the front-view dynamic radiograph (step S110). Processing of step S110 is the same as that described in step S16 of FIG. 5, so that the explanation thereof is to be cited.

If determined that the diameter of the trachea/bronchus region in the front view is expanded (YES in step S110), it is estimated as having tracheobronchomalacia (crescent type) (step S111) and the processing is shifted to step S113.

If determined that the diameter of the trachea/bronchus region in the front view is reduced (NO in step S110), it is estimated as having tracheobronchomalacia (circumferential type) (step S112) and the processing is shifted to step S113.

In a case where a plurality of estimation-target trachea/bronchus regions are extracted, the processing of step S102 to step S112 is executed for each region, and the processing is shifted to step S113 after completing the processing of steps S102 to S112 for all the regions.

In step S113, presence of stenosis and an estimated result of disorders are displayed on the display 34 (step S113), and the stenotic-state estimation processing F is ended. After completing the stenotic-state estimation processing F, the measured stenosis rate of the trachea/bronchus, the presence of stenosis, and the estimated result of the disorders are stored in the storage 32 by being associated with the dynamic radiograph.

The stenotic-state estimation processing A to F can be performed by replacing the diameter with the area instead of calculating the diameter or making determination based on the diameter.

When displaying the presence of stenotic state and the estimated result regarding the disorders on the display 34 in steps S19, S44, S59, S74, S94, and S113 described above, the controller 31 may also display the following information showing the stenotic state along therewith.

Figure 11:
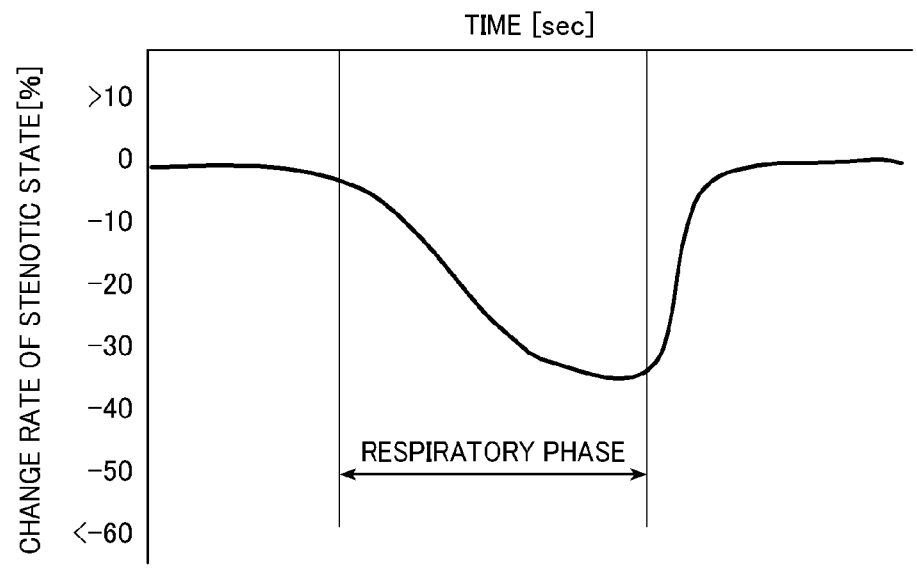
FIG. 11 is a graph showing chronological changes in the change rate of the stenotic state of the trachea/bronchus regions.

For example, as shown in FIG. 11, a graph showing the chronological change in the change rate of the stenotic state of the trachea/bronchus region may be generated and displayed on the display 34. Note here that the change rate of the stenotic state can be calculated by following (Expression 2). Parameter values are values of parameters (diameter (area) or concentration of the trachea/bronchus region, that is, feature amounts representing the stenotic state) used for estimation.

$$\text{Change rate of stenotic state} = (\text{parameter value of } n\text{-th frame} - \text{parameter value of 1st frame})/\text{parameter value of 1st frame} \quad \text{(Expression 2)}$$

Alternatively, a graph showing the chronological change in the parameter values may be displayed on the display 34. In that case, it is preferable to show where the expiratory phase is. The section of the expiratory phase can be specified as the section of the frame image from the point at which the lung field area is the maximum to the point at which the lung field area becomes the minimum Thereby, the user can grasp the chronological change in the state of the trachea/bronchus.

Figure 12:
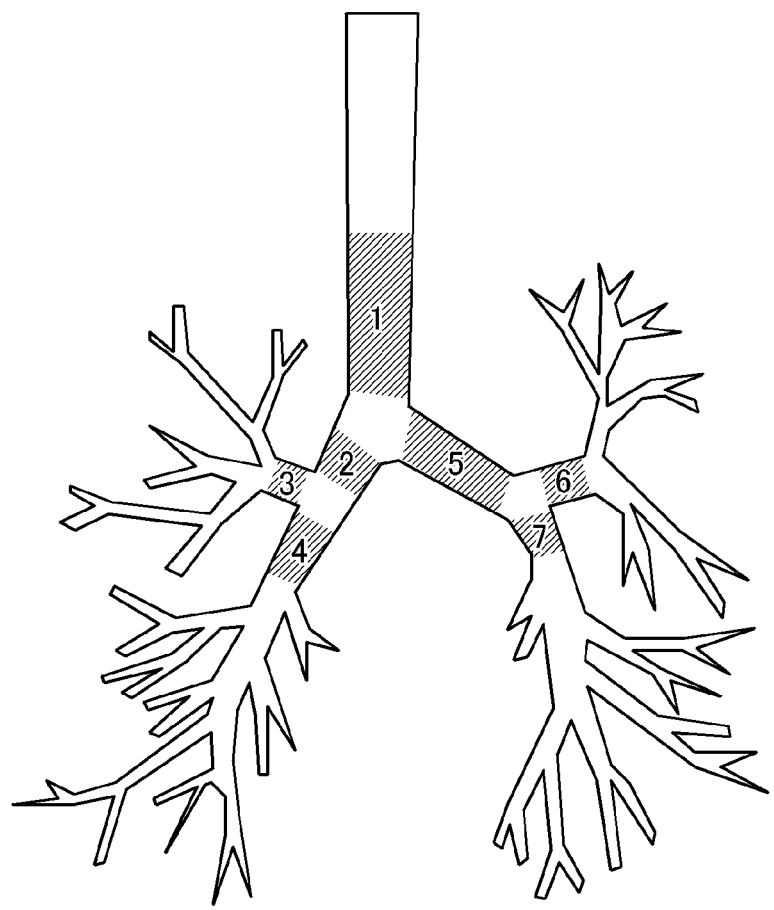
FIG. 12 is a visualized diagram of positions of the trachea/bronchus regions used for estimation of the stenotic states.
Figures 13, 14:
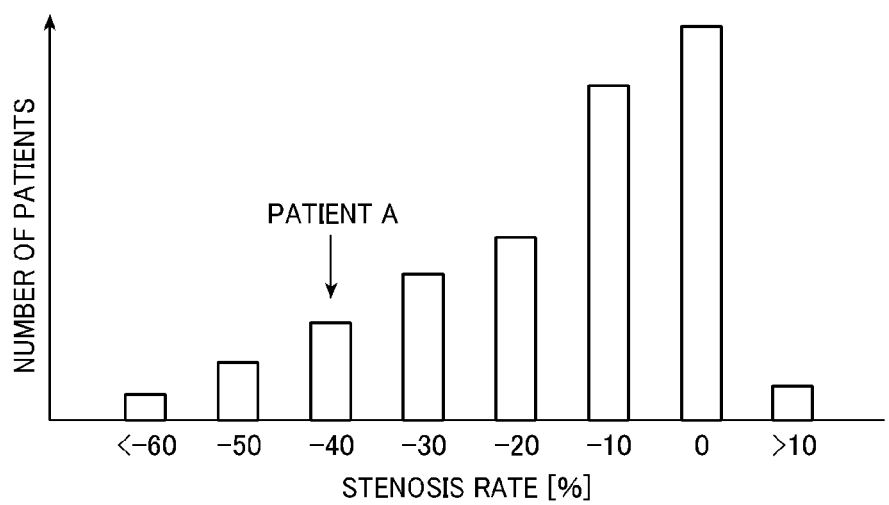
FIG. 13 is a table showing site names of the trachea/bronchus regions whose stenotic states are estimated, stenosis rates, area change amounts, and concentration change amounts in a form of list.
FIG. 14 is a graph showing a position of the stenosis rate measured this time on a histogram that shows a relation between the stenosis rates and the number of patients measured in the past.

Further, as shown in FIG. 12, positions of the trachea/bronchus used for estimation of the stenotic state may be visualized and displayed. For example, the positions of the trachea/bronchus used for estimation of the stenotic state may be colored in the representative frame image and displayed. Further, as shown in FIG. 13, the names of sites of the trachea/bronchus used for estimation of the stenotic state and the stenosis rates thereof may be displayed on a list. Thereby, the user can easily grasp the positions of the trachea/bronchus whose stenotic states are estimated and the degrees of the respective stenosis thereof. Further, along with the stenosis rates or instead of the stenosis rates, the change amount (maximum change amount) of the diameter (area) or concentration may be displayed. When displaying the change amount (maximum change amount) of the diameter (area) or concentration, it is preferable to add a plus sign when the diameter (area, concentration) is expanded (increased) and to add a minus sign when the diameter (area, concentration) is reduced (decreased).

Further, as shown in FIG. 14, a histogram showing the relation between the stenosis rates measured in the past and the number of patients may be generated, and the position (shown as patient A in FIG. 14) of the stenosis rate (stenosis rate of the subject) calculated from the dynamic radiograph this time may be displayed on the generated histogram. This makes it possible to grasp the degree of severity of the stenosis by comparing the stenosis rate of the subject with the past data. A threshold value for distinguishing normal/abnormal may be displayed on the histogram as well. Note that the stenosis rate may be replaced with the change rate of the diameter (area) or the concentration of the trachea/bronchus region.

Figure 15:
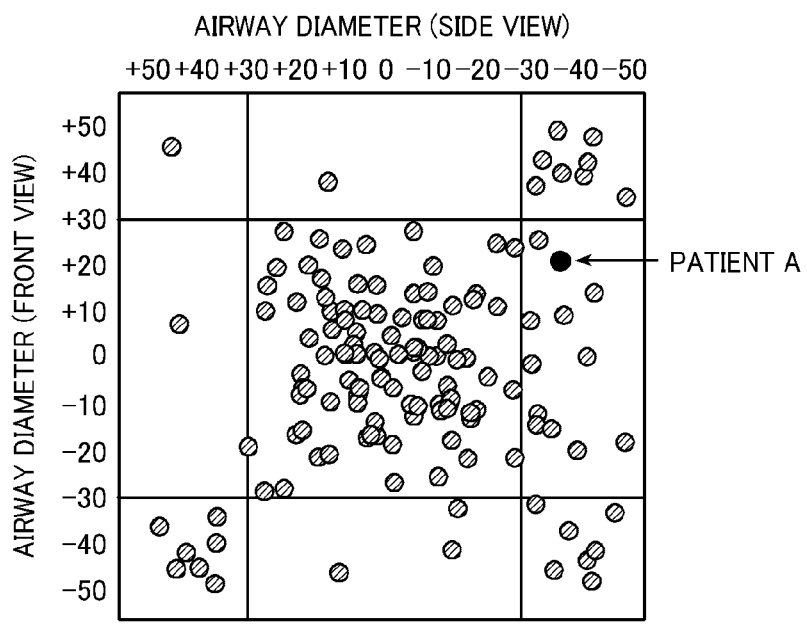
FIG. 15 is a chart showing a position of a change rate of the diameters of the front-view and side-view trachea/bronchus regions measured this time on a scatterplot of the change rates of the diameters of the front-view and side-view trachea/bronchus regions measured in the past.

Further, as shown in FIG. 15, a scatterplot of the change rates of the diameters (written as airway diameters in FIG. 15 and FIG. 16) of the trachea/bronchus regions of front view and side view measured in the past may be generated, and the position of the change rate of the diameter of the trachea/bronchus region of the front view and side view of the subject calculated from the dynamic radiographs this time may be plotted on the scatterplot (shown as patient A in FIG. 15) and displayed. This makes it possible to grasp the degree of severity of the stenosis of the trachea/bronchus of the subject by comparing the stenosis rate of the subject with the past data. Note that the diameter of the trachea/bronchus region may be replaced with the area or the concentration of the trachea/bronchus region.

Figure 16:
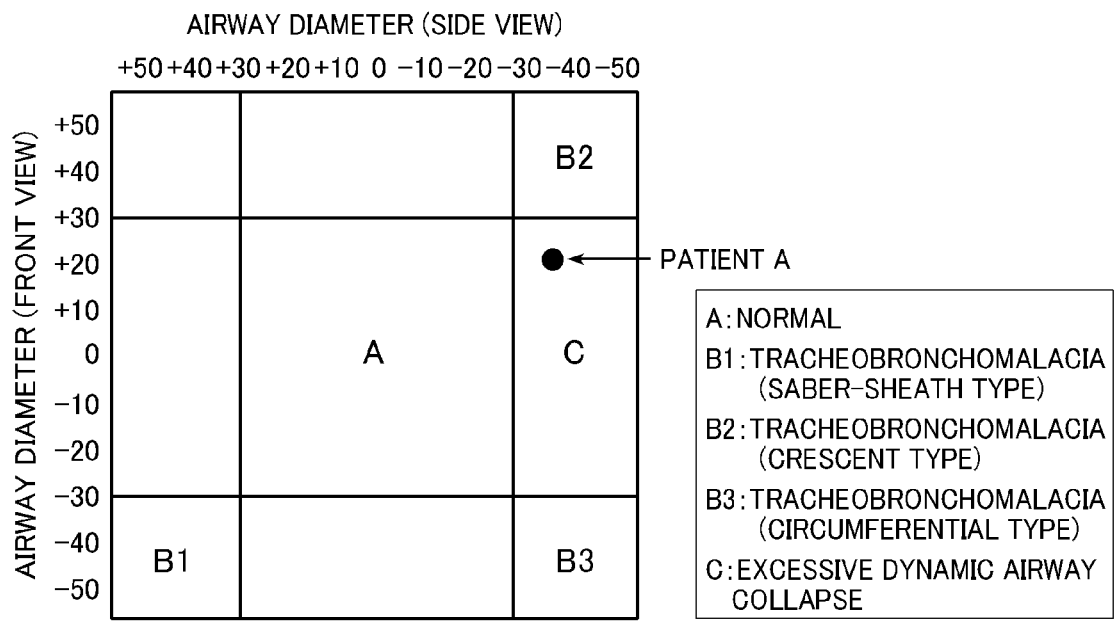
FIG. 16 is a chart showing a position of a change rate of the diameters of the front-view and side-view trachea/bronchus regions measured this time on a classification chart where a normal state and disorders are classified based on the change rates of the diameters of the front-view and side-view trachea/bronchus regions.

Further, as shown in FIG. 16, a classification chart where a normal state and disorders are classified based on the change rates of the diameters of the trachea/bronchus regions of front view and side view may be generated, and the position of the change rate of the diameter of the trachea/bronchus region of the front view and side view of the subject calculated from the dynamic radiographs this time may be plotted on the classification chart (shown as patient A in FIG. 16) and displayed. This makes it possible to easily estimate the stenotic state of the trachea/bronchus of the subject and the name of disorder. Note that the diameter of the trachea/bronchus region may be replaced with the area or the concentration of the trachea/bronchus region.

As described above, the controller 31 of the diagnosis console 3 analyzes the dynamic radiograph formed from the two-dimensional images acquired by radiographing dynamics of the subject including the trachea/bronchus to measure the feature amount representing the stenotic state of the trachea/bronchus, and estimates the stenotic state of the trachea/bronchus based on the result of measurement.

Therefore, it is possible to estimate the stenotic state of the trachea/bronchus with a still simpler examination method without performing an examination such as 4DCT examination that is high in the exposure dose and the cost.

For example, the controller 31 estimates the stenotic state of the trachea/bronchus based on at least one of the measurement results of the diameter, the area, and the concentration of the trachea/bronchus region in the dynamic radiograph. Therefore, it is possible to estimate the stenotic state of the trachea/bronchus from at least one of the diameter, the area, and the concentration of the trachea/bronchus region measured from the dynamic radiograph.

Moreover, the controller 31 further estimates the disorder of the trachea and/or bronchus, so that the user becomes capable of recognizing the disorder of the trachea and/or bronchus. As a result, it is possible to conduct an appropriate treatment suited for the disorder.

For example, when the dynamic radiograph is acquired by radiographing dynamics of the subject including the trachea and/or bronchus from one direction, the controller 31 can estimate the disorder of the trachea and/or the bronchus by measuring the diameter or the area and the concentration of the trachea region and/or the bronchus region from the dynamic radiograph.

Further, for example, when the dynamic radiographs are acquired by radiographing dynamics of the subject including the trachea and/or bronchus from two different directions, for example, the controller 31 can estimate the disorder of the trachea and/or the bronchus by measuring the diameter or the area of the trachea region and/or the bronchus region or measuring the concentration from both of the dynamic radiographs radiographed from the two directions. When the dynamic radiographs radiographed from the two directions are the images of the subject radiographed from the two directions from the front and the side, it is possible to estimate the disorder of the trachea and/or the bronchus with high precision.

By knowing the disorder of the trachea and/or the bronchus, it is possible to conduct an appropriate treatment suited for the disorder.

Further, the controller 31 can estimate the stenotic state with high precision by estimating the stenotic state of the trachea and/or the bronchus from the dynamic radiograph radiographed at a timing including the expiratory level.

Note that the content described in the embodiments simply shows a preferable example of the present invention, and the present invention is not limited thereto.

For example, while the case of estimating the stenotic state by using the dynamic radiographs radiographed from the directions from the front and/or the side is described in the embodiments, it is also possible to estimate the stenotic state by adding the dynamic radiograph radiographed from oblique directions. This makes it possible to perform estimation by increasing the information amount further such as irregular types of stenosis, so that it is possible to perform estimation with high precision.

Further, while the cases of estimating the stenotic state and the disorder by using one of flows of the stenotic-state estimation processing A to F shown in FIG. 5 to FIG. 10 are described in the embodiments, the present invention is not limited thereto. For example, the classification chart shown in FIG. 16 may be stored in advance in the storage 32, and the position of the change rate of the airway diameter (or the area, concentration) of front view and side view of the subject calculated from the dynamic radiographs this time (airway diameter (or area) and concentration in the case of one direction) may be plotted on the classification chart to estimate the stenotic state and the disorder of the subject.

Further, while the case of estimating the stenotic state and the disorder of the trachea/bronchus from the dynamic radiograph of the chest is described in the embodiment, there is no specific limit to be set as long as the radiographed images are of the subject including the trachea/bronchus. Further, it is also possible to use a plurality of still images acquired by continuously radiographing the subject including the trachea/bronchus at time intervals shorter than the respiratory cycle.

Further, for example, while the case of using a hard disc, a semiconductor nonvolatile memory, or the like as a computer readable medium of a program according to the present invention is disclosed in the explanations above, the present invention is not limited thereto. As another computer readable medium, it is possible to employ a removable recording medium such as CD-ROM. Further, as a medium for providing the data of the program according to the present invention via a communication line, a carrier wave is also employed.

For other detailed configurations and detailed actions of the image analysis apparatus, it is also possible to apply modification as appropriate without departing from the scope of the present invention.

Although embodiments of the present invention have been described and illustrated in detail, the disclosed embodiments are made for purposes of illustration and example only and not limitation. The scope of the present invention should be interpreted by terms of the appended claims

What is claimed is:

1. An image analysis apparatus, comprising a hardware processor that:
   analyzes at least one dynamic radiograph formed from a plurality of two-dimensional images acquired by radiographing dynamics of a subject including a trachea and/or a bronchus to measure feature amounts representing a stenotic state of the trachea and/or the bronchus, the feature amounts including a diameter and concentration of the trachea and/or bronchus; and
   estimates the stenotic state based on a result of the measurement of at least one of the diameter and the concentration of the trachea and/or the bronchus and identifies an individual specific disorder by selecting the individual specific disorder from a plurality of specific disorders of the trachea and/or the bronchus based on a result of the measurement of both of the diameter and the concentration of the trachea and/or the bronchus.

2. The image analysis apparatus according to claim 1, wherein, as the feature amounts, the hardware processor further measures an area of a trachea region and/or a bronchus region in the at least one dynamic radiograph.

3. The image analysis apparatus according to claim 1, wherein:
   the at least one dynamic radiograph is acquired by radiographing the dynamics of the subject including the trachea and/or the bronchus from one direction; and
   the hardware processor measures the diameter and the concentration of a trachea region and/or a bronchus region from the at least one dynamic radiograph.

4. The image analysis apparatus according to claim 1, wherein:
   the at least one dynamic radiograph comprises a plurality of dynamic radiographs acquired by radiographing the dynamics of the subject including the trachea and/or the bronchus from two different directions; and
   the hardware processor measures the diameter of a trachea region and/or a bronchus region in the dynamic radiographs and measures the concentration from both of the dynamic radiographs radiographed from the two directions.

5. The image analysis apparatus according to claim 4, wherein the dynamic radiographs are acquired by radiographing the subject from the two directions from front and side.

6. The image analysis apparatus according to claim 1, wherein the at least one dynamic radiograph is radiographed at a timing including expiration.

7. The image analysis apparatus according to claim 1, wherein the stenotic state is estimated by a change rate of the at least one of the diameter and the concentration of the trachea and/or the bronchus and the individual specific disorder of the trachea and/or the bronchus is identified based on a change rate of both of the diameter and the concentration of the trachea and/or the bronchus.

8. The image analysis apparatus according to claim 7, wherein the change rate of each feature amount of the feature amounts is based on (FAmax−FAmin)/FAmax,
   where FAmax is a maximum value of the each feature amount in the plurality of two-dimensional images and FAmin is a minimum value of the each feature amount in the plurality of two-dimensional images.

9. The image analysis apparatus according to claim 1, wherein the stenotic state is estimated by a change rate of the at least one of the diameter and the concentration of the trachea and/or the bronchus and the individual specific disorder of the trachea and/or the bronchus is identified based on a change rate of both of the diameter and the concentration of the trachea and/or the bronchus and whether at least one the diameter and the concentration of the trachea and/or the bronchus is expanded.

10. The image analysis apparatus according to claim 9, wherein the change rate of each feature amount of the feature amounts based on (FAmax−FAmin)/FAmax,
    where FAmax is a maximum value of the each feature amount in the plurality of two-dimensional images and FAmin is a minimum value of the each feature amount in the plurality of two-dimensional images.

11. The image analysis apparatus according to claim 1, wherein the at least one dynamic radiograph is acquired by radiographing the subject from a side view of the subject,
    the stenotic state is estimated based on a change rate of the diameter, and
    the specific disorder is identified as one of tracheobronchomalacia (saber-sheath type), tracheobronchomalacia (crescent type), tracheobronchomalacia (circumferential type), and excessive dynamic airway collapse based on at least one of whether the diameter is expanded, the change rate of the concentration, and whether the concentration is increased.

12. The image analysis apparatus according to claim 1, wherein the at least one dynamic radiograph is acquired by radiographing the subject from a front view of the subject,
    the stenotic state is estimated based on a change rate of the concentration, and
    the specific disorder is identified as one of tracheobronchomalacia (saber-sheath type), tracheobronchomalacia (crescent type), tracheobronchomalacia (circumferential type), and excessive dynamic airway collapse based on at least one of whether the concentration is increased, the change rate of the diameter, and whether the diameter is expanded.

13. The image analysis apparatus according to claim 1, wherein the at least one dynamic radiograph is acquired by radiographing the subject from a front view and a side view of the subject,
    the stenotic state is estimated based on a change rate of the diameter in the side view, and
    the specific disorder is identified as one of tracheobronchomalacia (saber-sheath type), tracheobronchomalacia (crescent type), tracheobronchomalacia (circumferential type), and excessive dynamic airway collapse based on at least one of whether the diameter in the side view is expanded, the change rate of the diameter in the front view, and whether the diameter in the front view is expanded.

14. The image analysis apparatus according to claim 1, wherein the at least one dynamic radiograph is acquired by radiographing the subject from a front view and a side view of the subject,
    the hardware processor further measures a sectional area of a trachea region and/or a bronchus region,
    the stenotic state is estimated based on a change rate of the sectional area, and
    the specific disorder is identified as one of tracheobronchomalacia (saber-sheath type), tracheobronchomalacia (crescent type), tracheobronchomalacia (circumferential type), and excessive dynamic airway collapse based on at least one of whether the diameter in the side view is expanded, the change rate of the diameter in the front view, and whether the diameter in the front view is expanded.

15. The image analysis apparatus according to claim 1, wherein the specific disorder is selected from a group of disorders consisting of tracheobronchomalacia (saber-sheath type), tracheobronchomalacia (crescent type), tracheobronchomalacia (circumferential type), and excessive dynamic airway collapse.

16. An image analysis apparatus, comprising a hardware processor that:
    analyzes a plurality of two-dimensional images acquired by continuously radiographing a subject including a trachea and/or a bronchus at a time interval shorter than a respiratory cycle to measure feature amounts representing a stenotic state of the trachea and/or the bronchus, the feature amounts including a diameter and concentration of the trachea and/or bronchus; and
    estimates the stenotic state based on a result of the measurement of at least one of the diameter and the concentration of the trachea and/or the bronchus and identifies an individual specific disorder by selecting the individual specific disorder from a plurality of specific disorders of the trachea and/or the bronchus based on a result of the measurement of both of the diameter and the concentration of the trachea and/or the bronchus.

17. The image analysis apparatus according to claim 16, wherein the specific disorder is selected from a group of disorders consisting of tracheobronchomalacia (saber-sheath type), tracheobronchomalacia (crescent type), tracheobronchomalacia (circumferential type), and excessive dynamic airway collapse.

18. An image analysis system, comprising:
    a radiographic imaging apparatus that acquires at least one dynamic radiograph formed from a plurality of two-dimensional images by radiographing dynamics of a subject including a trachea and/or a bronchus; and
    the image analysis apparatus according to claim 1.

19. An image analysis system, comprising:
    a radiographic imaging apparatus that acquires at least one dynamic radiograph formed from a plurality of two-dimensional images by radiographing dynamics of a subject including a trachea and/or a bronchus; and
    the image analysis apparatus according to claim 16.

20. A non-transitory storage medium storing a program that causes a computer to:
    analyze at least one dynamic radiograph formed from a plurality of two-dimensional images acquired by radiographing dynamics of a subject including a trachea and/or a bronchus to measure feature amounts representing a stenotic state of the trachea and/or the bronchus, the feature amounts including a diameter and concentration of the trachea and/or bronchus; and
    estimate the stenotic state based on a result of the measurement of at least one of the diameter and the concentration of the trachea and/or the bronchus and identify an individual specific disorder by selecting the individual specific disorder from a plurality of specific disorders of the trachea and/or the bronchus based on a result of the measurement of both of the diameter and the concentration of the trachea and/or the bronchus.

21. The non-transitory storage medium of claim 20, wherein the specific disorder is selected from a group of disorders consisting of tracheobronchomalacia (saber-sheath type), tracheobronchomalacia (crescent type), tracheobronchomalacia (circumferential type), and excessive dynamic airway collapse.

* * * * *